United States Patent [19]
Church et al.

[11] Patent Number: 5,288,468
[45] Date of Patent: Feb. 22, 1994

[54] PARALLEL SEQUENTIAL REACTOR

[75] Inventors: George M. Church, Brookline; Stephen G. Kieffer-Higgins, Dorchester, both of Mass.

[73] Assignee: The President and Fellows of Harvard College, Cambridge, Mass.

[21] Appl. No.: 970,650

[22] Filed: Oct. 30, 1992

Related U.S. Application Data

[63] Continuation of Ser. No. 705,308, May 24, 1991, abandoned.

[51] Int. Cl.[5] .................. C12M 1/00; G05B 13/00
[52] U.S. Cl. ......................... 422/116; 422/63; 435/287; 435/289; 935/88
[58] Field of Search .......... 422/63, 65, 67, 81, 422/110, 111, 116; 435/287, 288, 289; 436/47, 49, 527, 530; 935/88; 525/54.1, 54.11; 530/333, 334

[56] References Cited

U.S. PATENT DOCUMENTS

| | | | |
|---|---|---|---|
| 3,531,258 | 9/1970 | Merrifield et al. | 422/116 |
| 4,353,989 | 10/1982 | Bender et al. | 435/287 |
| 4,373,071 | 2/1983 | Itakura | 525/375 |
| 4,483,964 | 11/1984 | Urdea et al. | 422/116 |
| 4,517,338 | 5/1985 | Urdea et al. | 422/116 |
| 4,598,049 | 7/1986 | Zelinka et al. | 435/287 |
| 4,668,476 | 5/1987 | Bridgham et al. | 422/62 |
| 4,671,941 | 7/1987 | Niina et al. | 422/131 |
| 4,746,490 | 5/1988 | Saneii | 422/62 |
| 4,748,002 | 5/1988 | Neimark et al. | 422/116 |
| 4,952,518 | 8/1990 | Johnson et al. | 436/518 |

OTHER PUBLICATIONS

Alvarado-Urbina et al., Science 214:270-274, 1981.
Caruthers et al., Methods in Enzymology 154:287-313, 1987.
Djurhuss Matthes et al., Methods in Enzymology 154:250-285, 1987.
Fodor et al., Science 251:767-773, 1991.
Frank et al., Methods in Enzymology 154:221-249, 1987.
Geysen et al., Journal of Immunological Methods 102:259-274, 1987.
Hultman et al., Nucleosides and Nucleotides 7:629-638, 1988.
Geysen et al., Ciba Foundation Symposium 119:130-149, 1986.
Itakura et al., Ann. Rev. Biochem. 53:323-56, 1984.
Schnorrenberg and Lang, Proceedings of the Eleventh American Peptide Symposium, Jul. 9-14, 1989, Ed Rivier and Marshall, pp. 1029-1030, 1989.

Primary Examiner—Robert J. Warden
Assistant Examiner—T. A. Trembley
Attorney, Agent, or Firm—Fish & Richardson

[57] ABSTRACT

A reactor for sequentially modifying a molecule attached to a solid phase support, including: a plurality of substrate carriers, each substrate carrier capable of carrying a solid phase support to which a molecule to be modified can be attached; a plurality of reagent chambers, each capable of comprising a reagent for effecting a modification of the molecule; and means for individually bringing each of a plurality of chosen substrate carriers into a reagent-contact mode and a reagent-noncontact mode with each of a plurality of reagent chambers. Each of a plurality of the substrate carriers is capable of sequential contact with the contents of a plurality of the reagent chambers. The sequential contact is capable of resulting in the sequential modification of molecules attached to solid phase supports on the plurality of substrate carriers.

21 Claims, 12 Drawing Sheets

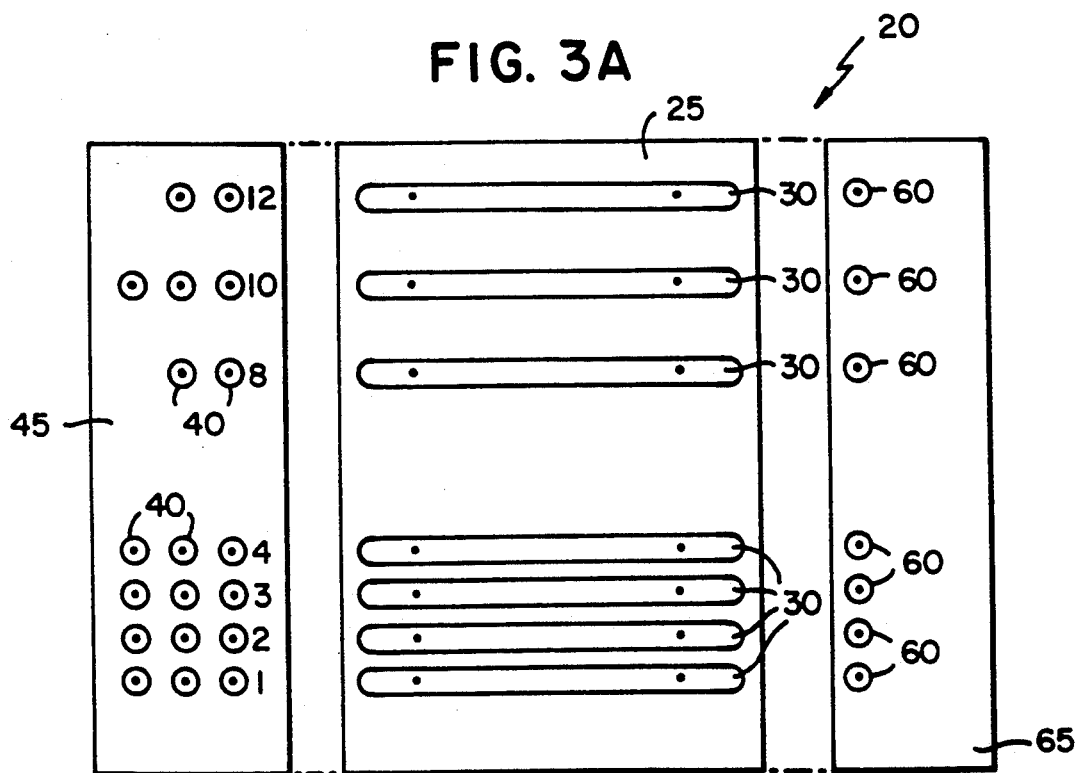
FIG. 3A
FIG. 3B
FIG. 3C
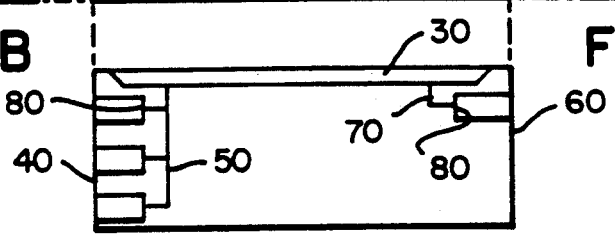
FIG. 3D

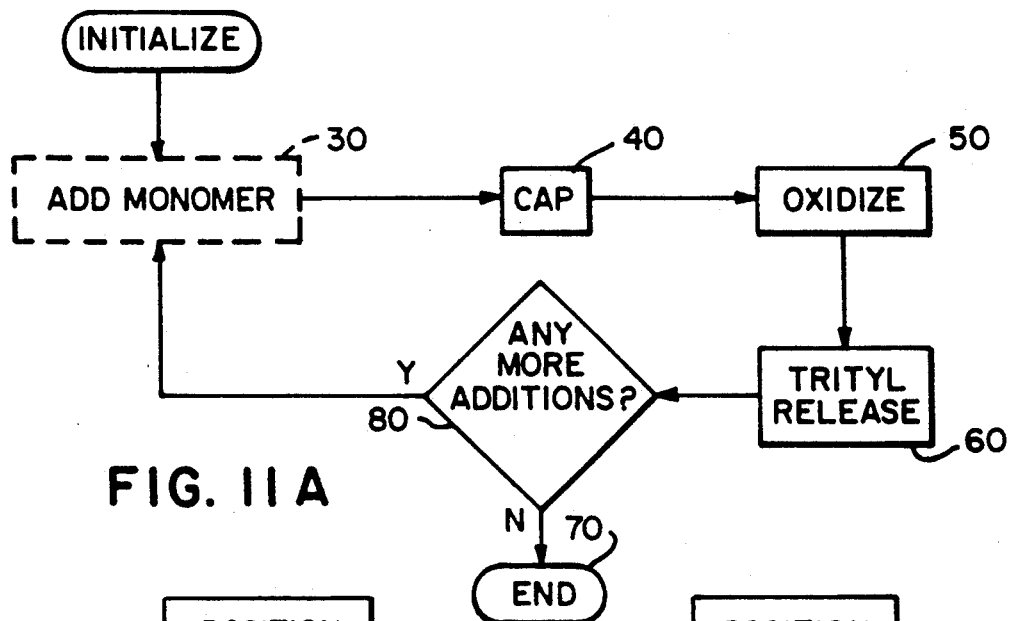
FIG. IIA
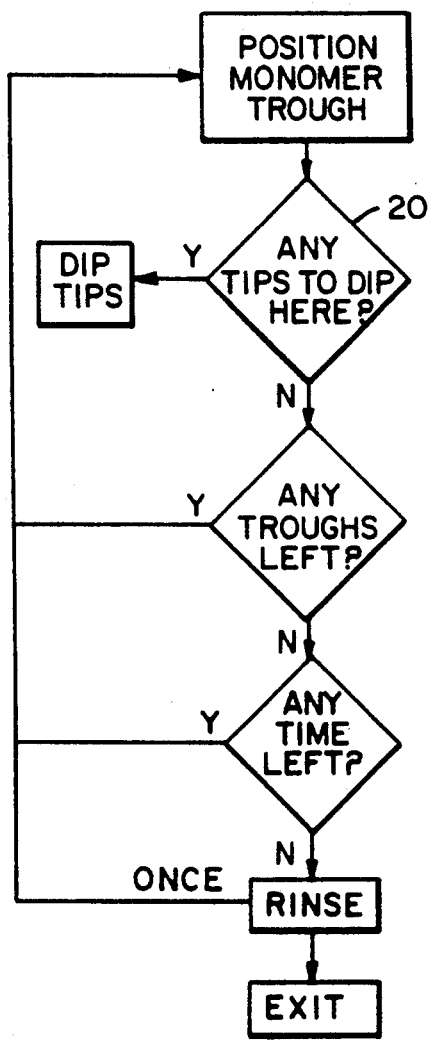
FIG. IIB
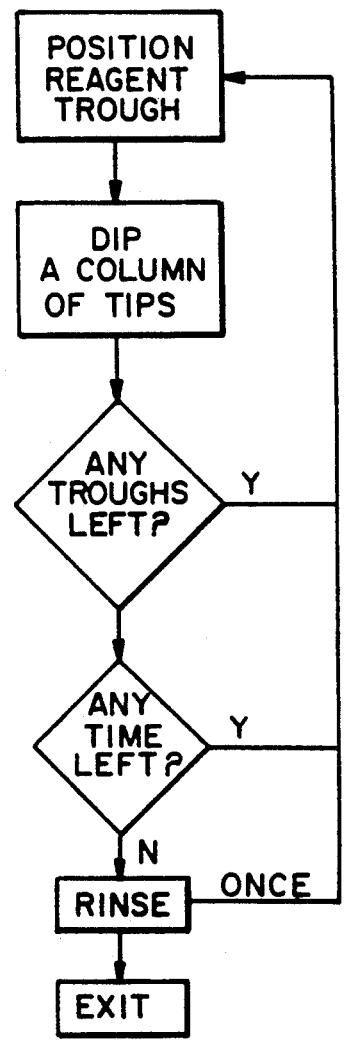
FIG. IIC

PARALLEL SEQUENTIAL REACTOR

This is a continuation of application Ser. No. 07/705,308, filed May 24, 1991, now abandoned.

BACKGROUND OF THE INVENTION

This invention relates to the simultaneous sequential modification of molecules located on more than one solid phase substrate and more particularly to the simultaneous synthesis of multiple polymeric molecules.

Recent advances in molecular biology and molecular medicine have generated substantial demand for manmade biological macromolecules, particularly peptides and nucleic acids.

SUMMARY OF THE INVENTION

In general, the invention features, a method and reactor for sequentially modifying a molecule attached to a solid phase support. The reactor includes: a plurality of substrate carriers, each substrate carrier capable of carrying a solid phase support to which a molecule to be modified can be attached; a plurality of reagent chambers, each capable of containing a reagent for effecting a modification of the molecule; and, means for individually bringing each of a plurality of chosen substrate carriers into a reagent-contact mode and into a reagent-non-contact mode with each of a plurality of chosen reagent chambers. Each of a plurality of the substrate carriers is capable of sequential contact with the contents of a plurality of the reagent chambers. Such sequential contact is capable of resulting in the sequential modification of molecules attached to the solid phase supports in the plurality of substrate carriers.

In preferred embodiments the reactor includes means for controlling the sequence in which the reagent chambers and the substrate carriers are brought into the reagent-contact mode; and, means for individually positioning each of a plurality of chosen substrate carriers in a reagent-contact mode and in a reagent-non-contact mode, and means for positioning each of a plurality of chosen reagent chambers relative to a chosen substrate carrier such that when the chosen substrate carrier is in the reagent-contact mode the chosen substrate carrier is in contact with the contents of a chosen reagent chamber and when the chosen substrate carrier is in the reagent-non-contact mode the chosen substrate carrier is not in contact with the contents of the chosen reagent chamber.

Other preferred embodiments include those in which: the reactor can simultaneously modify a first molecule on a first substrate carrier and a second molecule on a second substrate carrier; and the reactor can perform the simultaneous modifications in different reagent chambers.

Other preferred embodiments include those in which: the modification includes the addition of a monomeric subunit to a nucleic acid molecule, the substrate carriers are capable of carrying a solid phase support suitable to support the synthesis of the nucleic acid molecule, and the reactor includes sufficient reagent chambers to perform a sequence of reactions resulting in the synthesis of a nucleic acid molecule on one of the substrate carriers; the reactor can simultaneously synthesize a first oligomer on a first substrate carrier and a second oligomer on a second substrate carrier, the first and second oligomers differing in subunit sequence; and the reactor can simultaneously perform a reaction in the synthesis of the first oligomer and a reaction in the synthesis of the second oligomer in different reagent chambers.

Other preferred embodiments include those in which: the substrate carriers are capable of carrying a solid phase support suitable to support the synthesis of a protein molecule, the modification includes the addition of a monomeric subunit to the protein molecule, and the reactor includes sufficient substrate carriers to perform a sequence of reactions resulting in the synthesis of a protein molecule on one of the substrate carriers; the reactor can simultaneously synthesize a first protein on a first substrate carrier and a second peptide on a second substrate carrier, the first and second oligomers differing in subunit sequence; and the reactor can simultaneously perform a reaction in the synthesis of the first protein and a reaction in the synthesis of the second protein in different reagent chambers.

In other preferred embodiments the reactor includes means for supplying reagent to and removing reagent from a reagent chamber.

In other preferred embodiments the reactor includes: a computer to control the positioning of a plurality of the substrate carriers and the positioning of a plurality of the reagent chambers; the computer is programmed to effect a sequence of positionings of a first substrate carrier relative to a plurality of reagent chambers the sequence being capable of effecting a desired sequence of modifications of a polymeric molecule in a first substrate carrier; the computer is programmed to effect a sequence of positionings of a second substrate carrier relative to a plurality of reagent chambers the sequence being capable of effecting a desired sequence of modifications of a second polymeric molecule in a second substrate carrier; the computer is programmed such that the first polymeric molecule includes a different sequence of monomeric subunits than does the second polymeric molecule; the computer is programmed such that at least one reaction in the modification of the first polymeric molecule and one reaction in the modification of the second molecule are performed simultaneously; a computer is programmed such that the simultaneous reactions are performed in different reagent chambers; and the computer is programmed such that the simultaneous reaction are performed in the same reagent chamber.

In yet other embodiments the reactor includes: means for positioning each of a plurality of reagent chambers including a moveable carrier which includes a plurality of reagent chambers, the individual positioning means being positioned relative to the moveable carrier such that the action of an individual positioning means causes the transition from the reagent-non-contacting mode to the reagent-contacting mode of a chosen substrate carrier with respect to a chosen reagent chamber and movement of the moveable carrier establishes which of a plurality of reagent chambers is the chosen reagent chamber with respect to a chosen substrate carrier; the reactor can simultaneously modify a first molecule on a first substrate carrier and a second molecule on a second substrate carrier; the individual positioning means are positioned such that a first substrate carrier and a second substrate carrier can be simultaneously placed in the reagent contact mode with respect to a first chosen reagent carrier; and a third substrate chamber can simultaneously be placed in the reagent contact mode with respect to a second chosen reaction chamber.

In another aspect the invention features a nucleic acid oligomer synthesizer. The synthesizer includes: a plurality of moveable discrete surfaces suitable for supporting a substrate for the solid state synthesis of a nucleic acid oligomer; a moveable reagent chamber module which includes a plurality of reagent chambers, the module being capable of movement such that one of the chambers can be established as a chosen reagent chamber; and means for moving the discrete surfaces into contact with the contents of the reagent chambers. The plurality of discrete surfaces are positioned such that a first chosen surface can be placed in contact with the contents of a first chosen reagent chamber and a second chosen surface can be placed in contact with the contents of a second chosen reagent chamber. A reagent chamber is chosen by moving the module such that the chosen surfaces can be brought into contact with the contents of a reagent chamber chosen. The movement of each of a plurality of surfaces into contact with the contents of a reagent chamber is under individual control. A sequence of contacts between a surface and a plurality of reagent chambers is capable of synthesizing a nucleic acid oligomer on one of the surfaces.

Preferred embodiments include means for supplying reagent to and removing reagent from a reagent chamber.

Other preferred embodiments include those in which: the synthesizer includes a computer to control the positioning of a plurality of the surfaces and the positioning of a plurality of the reagent chambers; the computer is programmed to effect a sequence of contacts between a chosen surface and a plurality of chosen reagent chambers the sequence being capable of synthesizing a first oligomer on the chosen surface; the sequence is further capable of synthesizing a second oligomer on a second chosen surface; the computer is programmed such that the first oligomer comprises a different sequence of monomeric subunits than does the second oligomer; the computer is programmed such that at least one monomeric subunit of the first oligomer and one of the second oligomer are added simultaneously; the computer is programmed such that the simultaneous additions are performed in different reagent chambers; and the computer is programmed such that the simultaneous additions are performed in the same reagent chamber.

The invention also includes a method for the sequential modification of a molecule attached to a solid phase support. The method includes: supplying a plurality of substrate carriers, each substrate carrier capable of carrying a solid phase support to which a molecule to be modified can be attached; supplying a plurality of reagent chambers, each capable of containing a reagent for effecting a modification of the molecule; and supplying means for bringing positioning each of a plurality of chosen substrate carriers into a reagent-contact mode and into a reagent-non-contact mode with each of a plurality of chosen reagent carriers; and bringing each of a plurality of the substrate chambers into sequential contact with the contents of a plurality of the reagent chambers the sequential contacts being capable of resulting in the sequential modification of molecules attached to the solid phase supports on the plurality of substrate carriers.

Preferred embodiments include: controlling the sequence in which the reagent chambers and the substrate carriers are brought into the reagent-contact mode; and supplying means for individually positioning each of a plurality of chosen substrate carriers in a reagent-contact mode and in a reagent-non-contact mode and means for positioning each of a plurality of chosen reagent chambers relative to a chosen substrate carrier such that when the chosen substrate carrier is in the reagent-contact mode the chosen substrate carrier is in contact with the contents of a chosen reagent chamber and when the chosen substrate carrier is in the reagent-non-contact mode the chosen substrate carrier is not in contact with the contents of the chosen reagent chamber.

Other preferred embodiments include: simultaneously modifying a first molecule on a first substrate carrier and a second molecule on a second substrate carrier; and performing the simultaneous modifications in different reagent chambers.

Other preferred embodiments include: synthesizing a nucleic acid molecule, adding (as the modification) a monomeric subunit to the nucleic acid molecule, supplying substrate carriers capable of carrying a solid phase support suitable to support the synthesis of the nucleic acid molecule, and supplying sufficient reagent chambers to perform a sequence of reactions resulting in the synthesis of a nucleic acid molecule on one of the substrate carriers.

Other preferred embodiments include: simultaneously synthesizing a first oligomer in a first substrate carrier and a second oligomer in a second substrate carrier, the first and second oligomers differing in subunit sequence; and simultaneously performing a reaction in the synthesis of the first oligomer and a reaction in the synthesis of the second oligomer in different reagent carriers.

Other preferred embodiments include: synthesizing a protein molecule, adding (as the modification) a monomeric subunit to the protein molecule, supplying substrate carriers capable of carrying a solid phase support suitable to support the synthesis of a protein molecule, and supplying sufficient reagent chambers to perform a sequence of reactions resulting in the synthesis of a protein molecule on one of the substrate carriers.

Other preferred embodiments include: supplying means for supplying reagent to and removing reagent from a reagent chamber; controlling the positioning of a plurality of the substrate carriers and the positioning of a plurality of the reagent chambers with a computer; effecting, by the computer, a sequence of positionings of a first substrate carrier relative to a plurality of reagent chambers the sequence being capable of effecting a desired sequence of modifications of a polymeric molecule on a first substrate carrier; effecting, by the computer, a sequence of positionings of a second substrate carrier relative to a plurality of reagent chambers the sequence being capable of effecting a desired sequence of modifications of a second polymeric molecule on a second substrate carrier; and effecting, by the computer, a sequence of positionings such that the first polymeric molecule comprises a different sequence of monomeric subunits than does the second polymeric molecule; performing a sequence wherein at least one reaction in the modification of the first polymeric molecule and one reaction in the modification of the second molecule are performed simultaneously; performing a sequence wherein the simultaneous reactions are performed in different reagent chambers; and performing a sequence wherein the simultaneous reaction are performed in the same reagent chamber.

Yet other preferred embodiments include: providing the means for positioning each of a plurality of reagent chambers as a moveable carrier which includes a plurality of reagent chambers, the individual positioning means being positioned relative to the moveable carrier such that the action of an individual positioning means causes the transition from the reagent non-contacting mode to the reagent-contacting mode of a chosen substrate carrier with respect to a chosen reagent chamber, and moving the moveable carrier to establish which of a plurality of reagent chambers is the chosen reagent chamber with respect to a chosen substrate carrier; and simultaneously modifying a first molecule on a first substrate carrier and a second molecule on a second substrate carrier; positioning the individual positioning means such that a first substrate carrier and a second substrate carrier can be simultaneously placed in the reagent contact mode with respect to a first chosen reagent chamber; positioning the array of individual positioning means such that a first substrate chamber and a second substrate chamber can be simultaneously placed in the reagent contact mode with respect to a first reagent chamber; simultaneously positioning a third substrate carrier in the reagent contact mode with respect to a second reagent chamber.

Other preferred embodiments include: simultaneously synthesizing a first protein on a first substrate carrier and a second peptide on a second substrate carrier, the first and second oligomers differing in subunit sequence; and simultaneously perform a reaction in the synthesis of the first protein and a reaction in the synthesis of the second protein in different reagent chambers.

The invention also includes a method of synthesizing a nucleic acid oligomer. The method includes: supplying a plurality of moveable discrete surfaces suitable for supporting a substrate for the solid state synthesis of a nucleic acid oligomer; supplying a moveable reagent chamber module comprising a plurality of reagent chambers, the module being capable of movement such that a particular chamber can be established as a chosen chamber; supplying means for moving the discrete surfaces into contact with the contents of the reagent chambers, the plurality of discrete surfaces being positioned such that a first chosen surface can be placed in contact with the contents of a first chosen reagent chamber and a second chosen surface can be placed in contact with the contents of a second reagent chamber; choosing a reagent chamber, by moving the module such that the chosen surfaces can be brought into contact with the contents of a chosen reagent chamber; and moving each of a plurality of individually controllable surfaces into contact with the contents of a plurality of reagent chambers to effect a sequence of contacts between surfaces and reagent chambers capable of synthesizing a nucleic acid molecule on one of the surfaces.

Preferred embodiments include: supplying means for supplying reagent to and removing reagent from a reagent chamber.

Other preferred embodiments include: supplying a computer to control the positioning of a plurality of the surfaces and the positioning of a plurality of the reagent chambers; effecting, by computer, a sequence of contact between a chosen surface and a plurality of chosen reagent chambers the sequence being capable of synthesizing a first oligomer on the chosen surface effecting, by computer, a sequence further capable of synthesizing a second oligomer preferably with a different sequence from the first oligomer on a second chosen surface; effecting, by computer, a sequence in which at least one monomeric subunit of the first oligomer and one of the second oligomer are added simultaneously in the same or in different reagent chambers.

The invention also includes modified molecules, e.g., nucleic acid oligomers or protein molecules, made by the methods described herein.

Sequentially modifying, as used herein, means performing at least two modifications, one of which is initiated prior to the other.

Modifying a molecule, as used herein, means effecting a chemical change in the molecule, e.g., breaking a covalent or noncovalent bond in the molecule, adding or removing a component or monomeric subunit, or cleaving a molecule from a substrate, or changing the environment of the molecule, e.g., by altering the purity or concentration of the molecule.

Simultaneous, as used herein, means overlapping in time.

A reaction, as used herein, is an event in which a molecule is modified.

Methods and devices of the invention provide for the rapid, easy, and economical simultaneous synthesis of multiple DNA oligomers. The invention does not require laborious packing of columns or sorting of paper substrates and minimizes the waste of reagents. Large numbers of oligomers are produced simultaneously and physically separated from one another.

The invention is particularly useful where 1–500 pmol of DNA is desired, e.g., for use in DNA sequencing, hybridization assays, diagnostic procedures, polymerase chain reaction procedures, gene synthesis, and site directed mutagenesis.

Other features and advantages of the invention will be apparent from the following detailed description and from the claims.

BRIEF DESCRIPTION OF THE DRAWINGS

The drawings are first described.

Drawings

FIG. 3A is a top elevational view of the trough module;

FIG. 3B is a front elevational view of the trough module;

FIG. 3C is a rear elevational view of the trough module;

FIG. 3D is an end elevational view of the trough module;

FIG. 11 is a flow chart for a computer program suitable for use with the reactor.

DNA Synthesizer: Overview

A DNA synthesizer capable of the simultaneous synthesis of a large number of different oligomers is described below. The device includes six discrete surfaces on which oligomers can be synthesized. (Although the embodiment discussed here has six synthetic surfaces it is easily modified, as described below, to incorporate many more surfaces, thus allowing the simultaneous synthesis of many more oligomers.) The surfaces have a solid-phase support suitable for the synthesis of DNA adhered to them. The device also includes a number of reagent chambers which hold reagents used in the synthetic reactions. The movement of a surface in and out of a sequence of reagent chambers results in the proper sequence of reactions for the synthesis of an oligomer of desired sequence. By movement of the individual surfaces and the chambers the device allows individual control over the contact of each surface with each reagent chamber.

Each discrete surface is carried on the tip of a solenoid-piston assembly, with the solenoid action capable of raising or lowering the tip. The solenoid-piston assemblies are arranged in an array of rows above an array of reagent chambers. The reagent chambers consist of troughs cut in the surface of a block of inert plastic. The block can be moved, by a stepping motor, so as to allow a row of solenoid borne tips access to a given reagent trough. When lowered, a surface (or tip) dips into the contents of the reagent chamber positioned beneath it.

The tips in a row are, by the action of the solenoids, either dipped into the trough below them or held above the trough and thus not dipped into the trough, depending on whether the sequence of the molecule being constructed requires contact with the reagent in the trough. Tips in adjacent rows are positioned above respective adjacent troughs. Dipping of surfaces is controlled individually and simultaneously, thus different reactions, i.e., reactions in different troughs, occur simultaneously.

The device also includes a system of valves, lines, and reservoirs to supply the troughs with reagents, a motor to move the trough block, and a computer and interface to control the action of the solenoids, valves, trough block. The computer, which is programmed with the sequence of the oligomer to be synthesized on each tip, generates instructions for the proper sequence of dipping, trough movement, and valve control, to effect the desired synthetic reactions, i.e., to effect the simultaneous synthesis of specific oligomers on specific surfaces.

Structure and Operation

Figure 1:
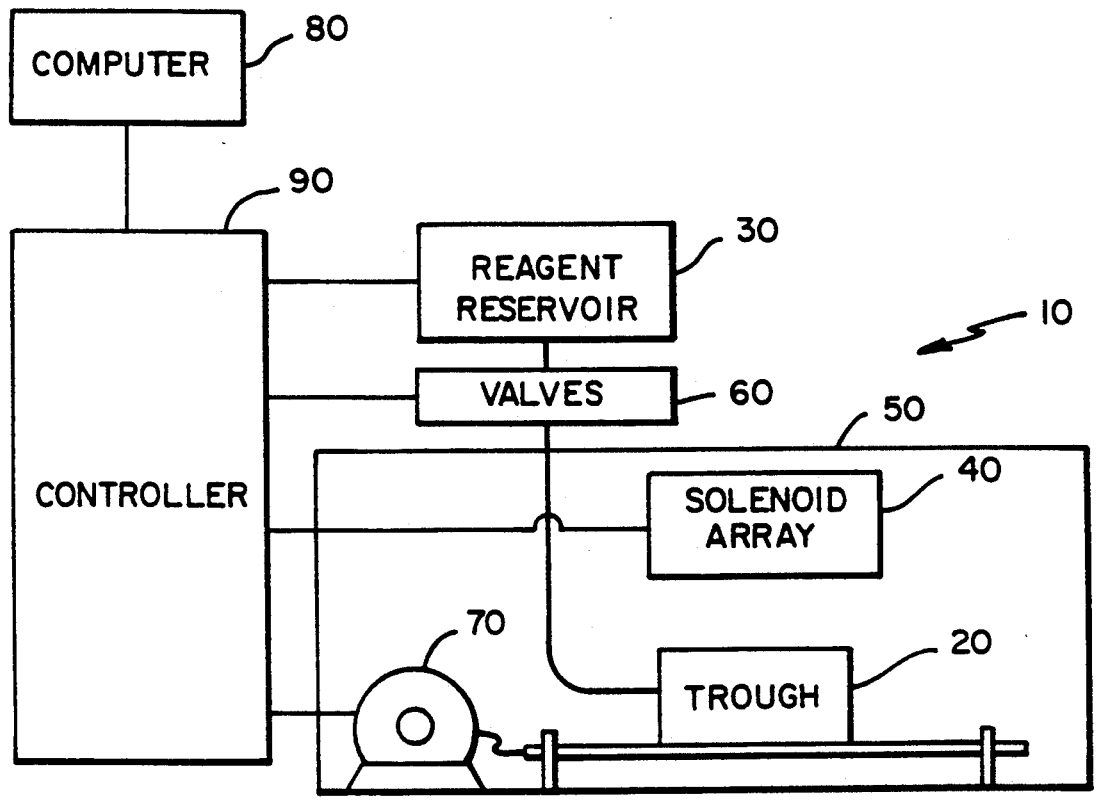
FIG. 1 is a combined block-pictorial diagram of one embodiment of the reactor of the present invention.

As shown in FIG. 1, and described more fully below, the principle components of the automated synthesizer 10 are trough assembly 20, reagent reservoir and drive system 30, solenoid array 40, gastight enclosure 50, valve block 60, motor 70, computer 80 and controller 90.

Trough Assembly

The trough assembly provides reagent troughs which can be movably positioned beneath an array of solenoid mounted synthetic surfaces. Reagent troughs are located on a carrier block which is moved by a stepping motor.

Figure 2:
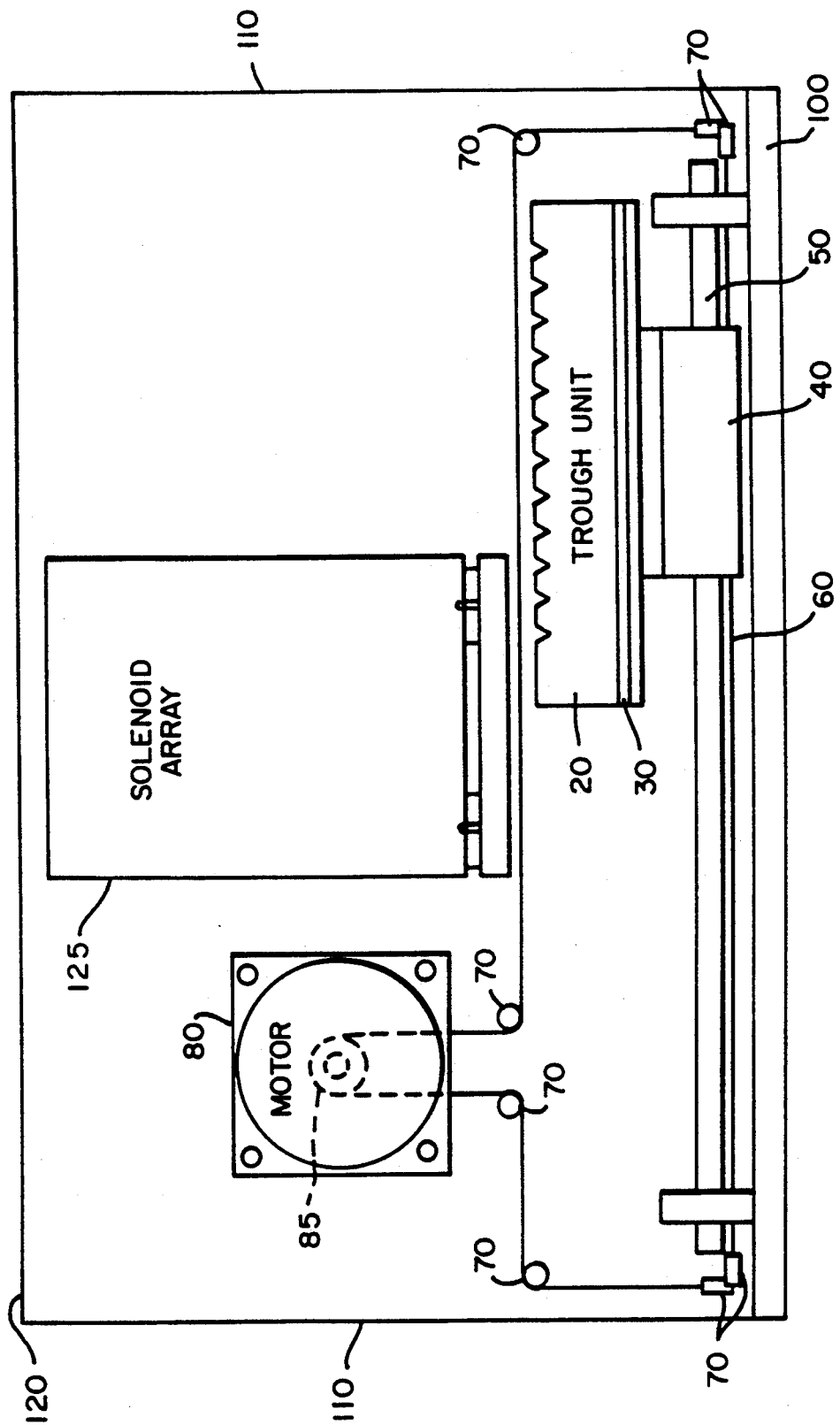
FIG. 2 is a cross-sectional view of a portion of the reactor.

With reference to FIG. 2, the trough assembly includes trough module 20, mounting assembly 110, pillow blocks 120, travel rails 130, drive belt 140, pulleys 150, and stepping motor 160.

The trough module, shown in FIG. 3, was milled from a solid block of polypropylene, although any similar inert material is suitable. The trough module 20 is 5 inches in length, 1.275 inches deep, and 3.375 inches wide. The troughs 170, which are milled in the top face 175 (FIG. 3A) of trough module 20, are numbered 12, 10, 8, 4, 3, 2, 1. With the exception of trough No. 8, the troughs are milled to a 60° angle at the base and are 5 mm deep. Trough No. 8 is round bottomed and 8 mm deep to facilitate a higher volume of reagent flow during the detritylation step. The troughs 170 are spaced 9 mm on-center, so as to be compatible with the spacing found in commercially available 96 well laboratory equipment. Reagent inlet ports 180, located on the front face 185 (FIG. 3B) of trough module 20, and reagent delivery lines 300 allow delivery of reagents to the troughs 170. The reagent inlet ports 180 are tapped for standard ¼" 28 connections. The reagent exhaust ports 210, located on the back face 215 (FIG. 3C) of trough module 20, and reagent exhaust lines 220 allow removal of reagents from the troughs 170. The reagent exhaust ports 210 are tapped for standard ¼" 28 connections.

As shown in FIG. 3D, the bottom surface 230 of the reagent inlet and exhaust ports should be flat, to allow a good seal standard ¼" 28 connectors. All ports and lines should be constructed so as to minimize the dead volume of the system while still allowing adequate flow rates. Their surfaces should be smooth to facilitate washing and to minimize contamination.

Figure 4:
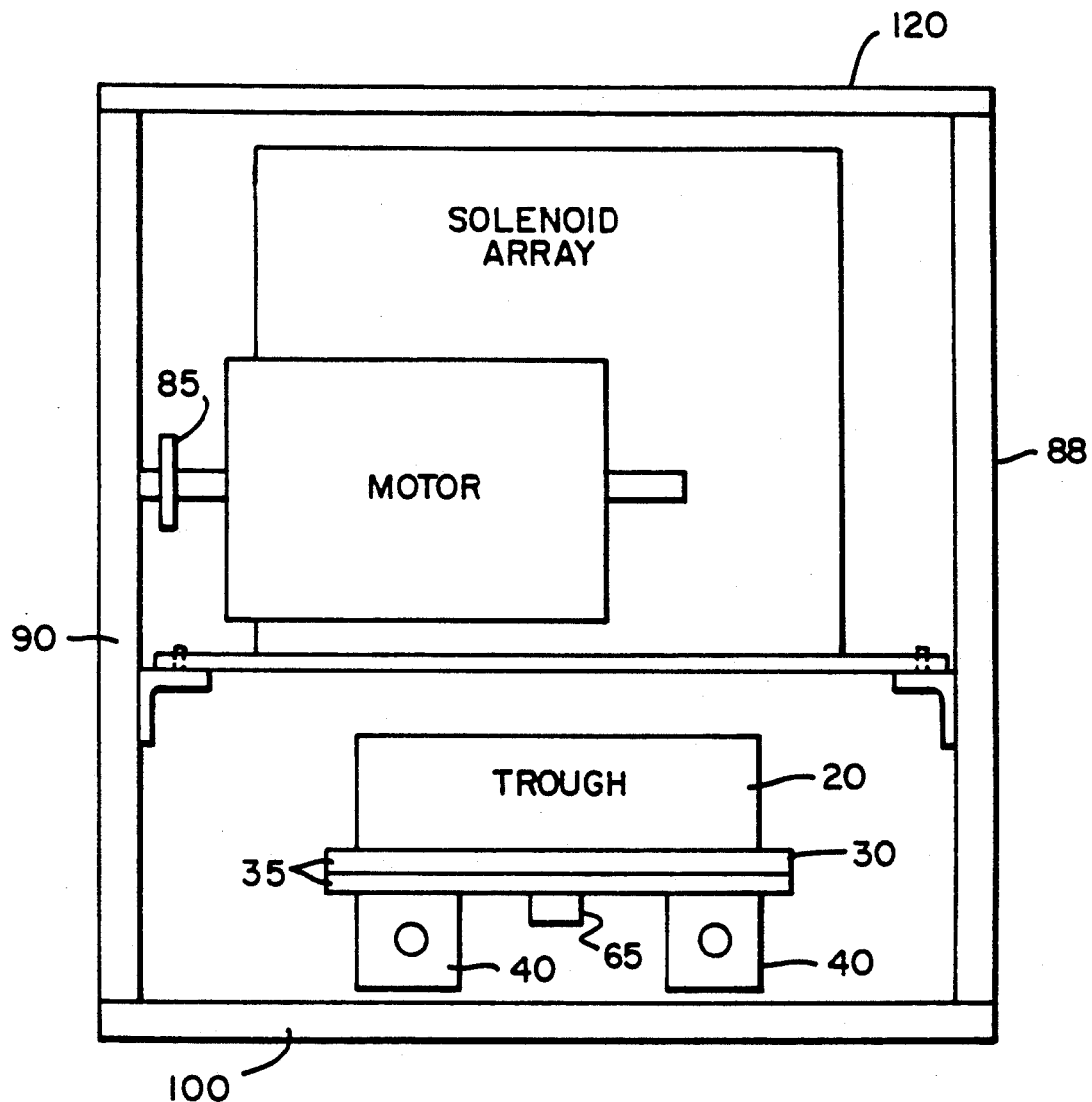
FIG. 4 is an end view of a portion of the reactor.
Figure 5:
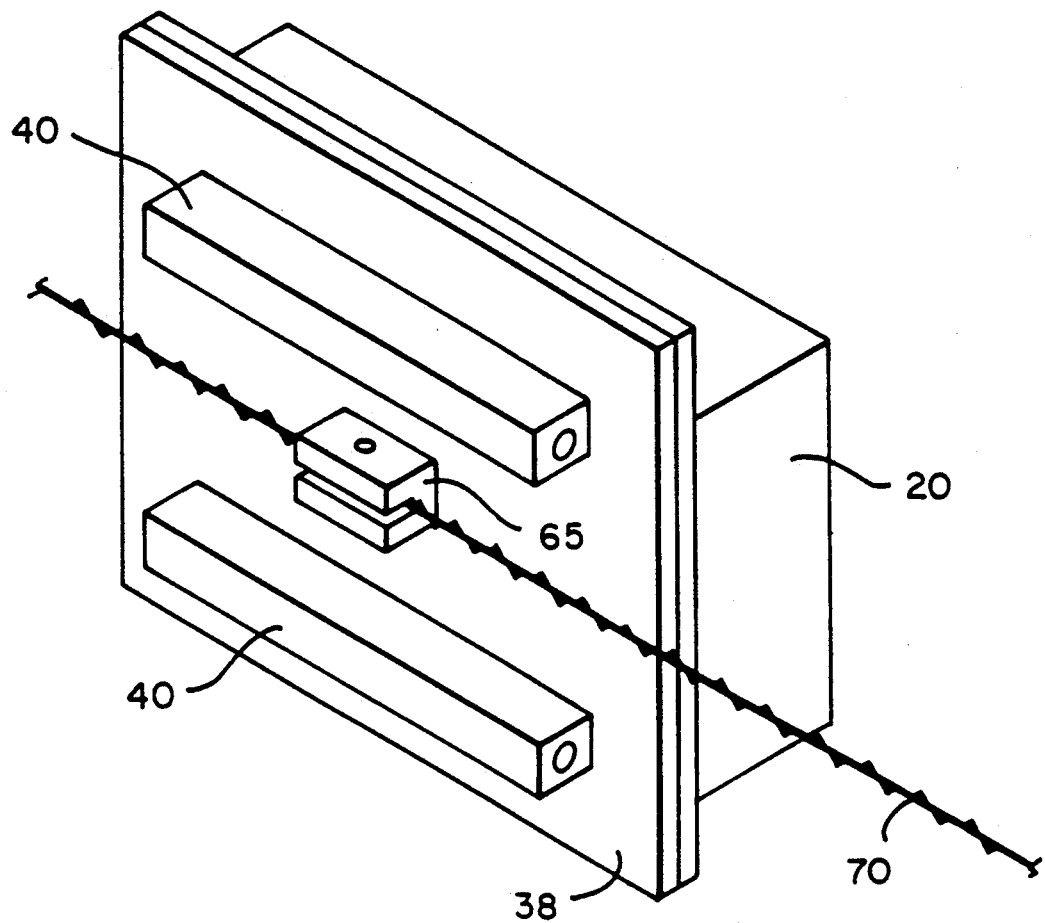
FIG. 5 is a bottom perspective view of the trough module and associated structures.

As shown in FIGS. 2, 4, and 5, the trough module 20 is mounted on pillow blocks 120 (TWN-4-ADJ super ball bushing twin pillow block, Atlantic/Tracy, Inc.) to allow travel of the trough module 20 on the travel rails 130. The mounting assembly 110 includes two ⅛ inch aluminum plates 240, to which the trough module 20 is rigidly but removably mounted. Pillow blocks 120 are mounted on the underside 250 of the mounting assembly 110. The travel rails 130 pass through the pillow blocs 120. The drive belt 140 is fixed rigidly to the drive belt anchor 260 and is held in position by pulleys 150. Angular displacement of the main drive pulley 270 of the stepping motor 160 is translated by the drive belt 140 into transverse displacement, along the travel rails 130, of the trough module 20.

The main drive pulley 170 is located as close to the back plate 280 of the gas tight enclosure as possible. The drive belt 140 is routed so that it will not interfere with the solenoid array, the reagent supply or exhaust lines connected to the trough unit, or other elements of the device. The drive belt 140 is positioned as closely to the ends of the gastight enclosure as possible and as close to the base plate 290 as possible, and is routed along the centerline of the baseplate 290 to the trough unit. Kill switches are appropriately placed so as to limit the travel of the trough unit and preventing it from moving into the glass endplates 300.

Reagent reservoir and drive system

The reagent reservoir and drive system provides for the supply and removal of reagents, e.g., monomer, oxidizer, and rinsing agents, to the monomer troughs.

Figure 6:
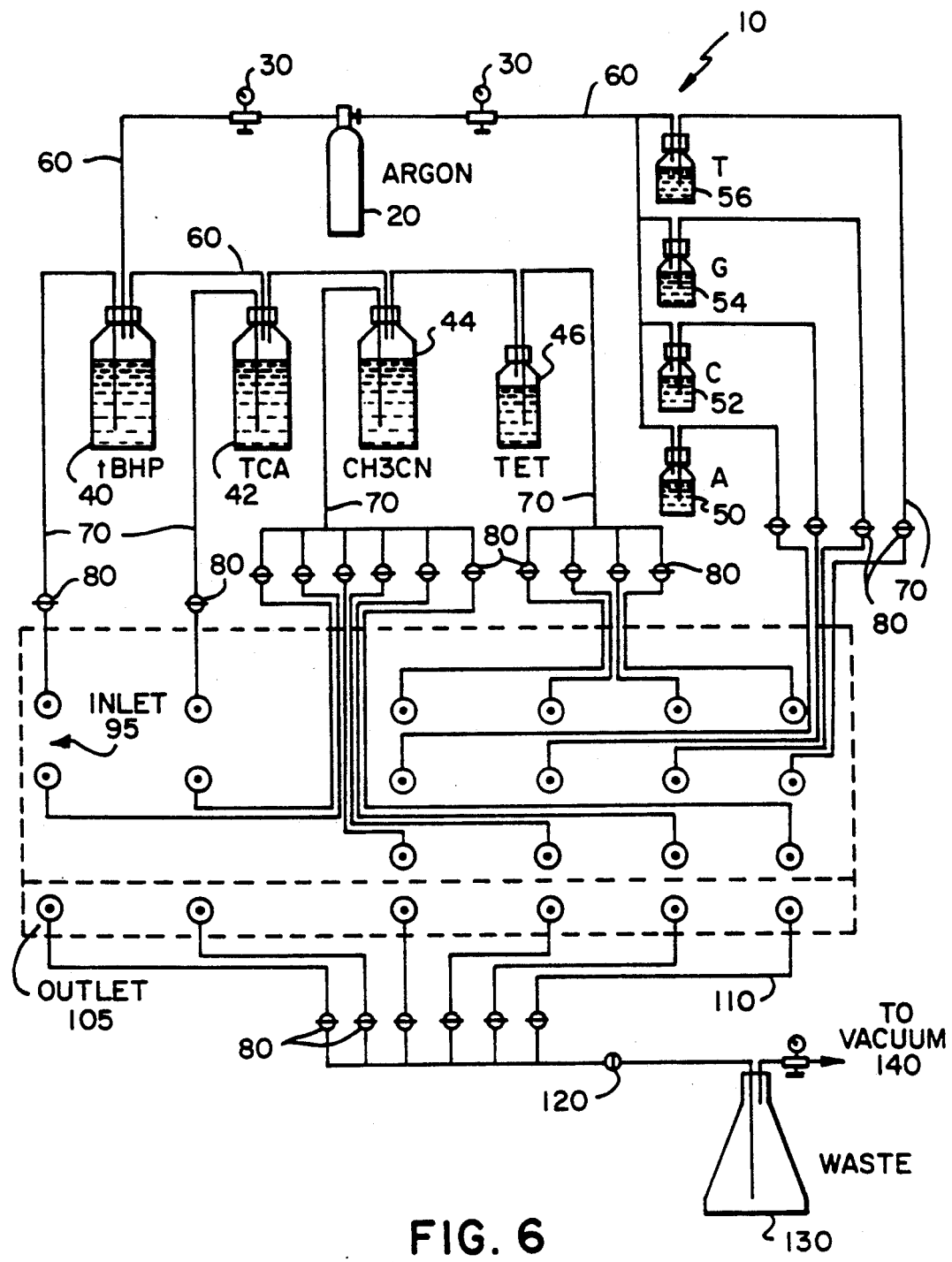
FIG. 6 is a diagram of the reagent reservoir and drive system.

As shown in FIG. 6, the reagent reservoir and drive system 310 includes, gas source 320, metering valves 330, reagent reservoirs 340, 342, 344 and 346, monomer reservoirs 350, 352, 354, and 356, gas lines 360, delivery lines 370, two-way valves 380, reagent inlet connectors 390 (connected to the front face 185 of the trough module), reagent exhaust connectors 400 (connected to the backface 215 of the trough module), exhaust lines 410, three way valve 420, vacuum trap 430, and vacuum source 440.

Gas pressure from gas source 320 provides the motive force for the transfer of reagents from their reservoirs, through the delivery lines, to the reagent inlet connectors (and thus to the troughs of the trough module). Motive force for the removal of reagent or monomer from a trough is provided by a vacuum source. The delivery or removal of a reagent is controlled by opening and closing appropriate subsets of valves. As described below, the operation of the valves is under computer control.

Argon is a suitable inert gas for use in the reagent reservoir and drive system. A standard 2-stage regulator is used to release ultra-pure argon from the supply tank at approximately 10 psi. The lines supplying argon to the monomer reservoirs are set at 6 psi. The monomers and tetrazole are delivered from the bottles they are shipped in. Argon pressure is delivered to them through a 20 gauge 1½" needle attached to a male luer(w/lock)-¼"24 adaptor connected to the appropriate general valve connector. The other reagents are stored in Kontes HPLC/synthesizer reservoirs. Argon is delivered to these reservoirs at 3 psi directly to inlet ports in the caps of the reservoirs.

Solenoids and solenoid array

The lower tips of the solenoid piston assemblies (on which the synthetics surfaces are mounted) can be dipped into the reagent troughs by the action of the solenoids. The positioning of the solenoid array, together with the allowable travel of the trough module, insure that each solenoid row has access to each trough on the trough module.

Figure 7:
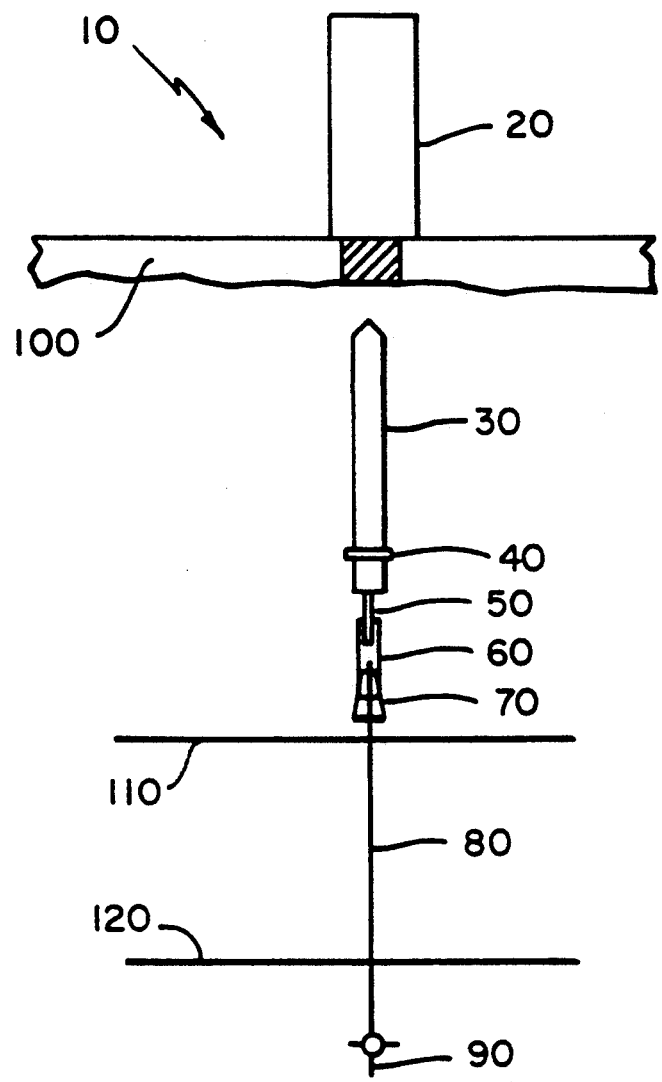
FIG. 7 is a partially exploded side elevational view of a solenoid-piston-reagent tip assembly.

A solenoid-piston-reagent pin assembly 510 is shown in FIG. 7. The assembly includes a solenoid 520, piston 530, retaining ring 540, connecting rod 550, adaptor 560, pin socket 570, pin 580, and reagent tip 590.

A Guardian T 3.5×9-C12D, 12 volt DC continuous duty tubular solenoid is a suitable solenoid. The retaining ring 540 can be fabricated from polypropylene, e.g., a one millimeter thick slice cut from a Rainin RT96 pipette tip. The connecting rod 550 is a plastic shaft which can be fabricated, for example, from the positive displacement piston of a Gilson CP-250 pipette. The flexible adaptor 560 can be fabricated from a piece of flexible tubing, for example, Cole-Parmer 1/32×3/32 C-flex tubing. The pin socket 570 can be fabricated from the distal six millimeters of a Rainin RT96 pipette tip. The pin 580 is a steel rod and can be fabricated from the displacement piston of a Gilson CP-50 pipette. The reagent tip 590 is made of polypropylene. The proximal fitting from the steel displacement piston of a Gilson CP-50 pipette can be used for a reagent tip.

The solenoid assemblies 520 are mounted in solenoid array frame 600. The frame 600 can be fabricated from a Rainin RT96 pipette box. The solenoid assemblies 520 are positioned in an array such that the longitudinal axis of the pistons are aligned with the spacing found in standard 96-well titre plates. (Standard 96 well-plates have an 8×12 array of wells. The wells are spaced 9 mm on-center). The solenoids should be positioned in a staggered, i.e., a two tier, configuration, because the solenoid diameter is too great to allow them to be packed adjacently, i.e., at the same level. The two tier arrangement also allows improved heat dissipation. Piston 530 is inserted into solenoid 520. Retaining ring 540 is fitted onto piston 530. Connecting rod 550 links flexible adapter 560 to piston 530 and on the other end to pin socket 570. Pin 580 fits removably into pin socket 570. Retaining ring 540 prevents the piston from seating fully on energizing of the solenoid 520. If allowed to seat fully residual magnetism prevents the piston from descending when the power is removed. Beneath the piston assembly upper guide plate 610 and lower guide plate 620 align the reagent pin 580 and direct it to the trough. Guideplates 610, 620 are fixed rigidly with respect to solenoid array frame 600. A clearance of about 1 mm exists between the tip and the top surface of the trough when the solenoids are energized. The upper guide plate 610 prevents the piston from falling out of the solenoid and determines the magnitude of piston travel. Total piston travel is about 8 mm.

Oligomers are synthesized on a solid phase substrate adhered to the reagent tips. Any suitable solid phase substrate, e.g., glass fiber, cellulose, or controlled pore glass beads, can be used. Commercially available controlled pore derivatized beads (to which A, T, G, or C monomer has been attached) used in column based DNA synthesis, e.g., those available from ABI (e.g., A controlled pore glass ABI part number 400386, C controlled pore glass ABI part number 300387, G controlled pore glass ABI part number 400388, and T controlled pore glass ABI part number 400389) or, Milligen, are particularly convenient for use with the device.

The beads are adhered to the reagent tips by heating the reagent tip until it is just molten then forcing the heated tip into a shallow container filled with the appropriate bead. When beads coupled to a given monomer are used for the synthesis of a molecule that monomer forms the first subunit, in the 3'-5' direction of the molecule.

Gastight enclosure

The gastight enclosure provides a solid base on which other components, e.g., the motor, travel rails, and solenoid array can be mounted and isolates the reagent tips and reagents from the atmosphere.

With reference to FIGS. 2 and 4 the gastight enclosure has front plate 302, back plate 280, and base plate 290, fabricated from 0.3125" aluminum, and endplates 300 and top plate 306 fabricated from 0.3125" glass. Silicone gaskets are glued to the glass plates, and the glass plates clamped to the aluminum structure to provide a gastight environment. A humidity meter (not shown) is attached to the top plate with its probe snaked between the aluminum side and top silicone seal. Lines delivering fresh reagent enter the device through the front plate 302. The vacuum (exhaust) line, argon purge lines (not shown), and electrical connections, pass through the back plate 280 and the motor is attached to the back plate 280. The trough unit travels on rails attached to the base plate 290. The solenoid array 304 rests on supports that are connected to the front 302 and back 280 plates. The solenoid array 304 is firmly seated yet removable.

The entire enclosure can be purged of atmospheric gases by argon delivered through a regulator.

Valve Block

The valve block provides valves which control the flow of reagents to and from the reagent troughs.

The valve block consists of 24 12 VDC 2-way teflon valves (GV#2-17-900, General Valve Corp.) which control the flow of monomers and other agents to and from the trough module and a single 3-way teflon valve (GV#1-17-900 General Valve Corp.) which controls exhaust vacuum. The 2-way valves are closed when not energized and open when energized All 2-way exhaust valves (Omega relay #7-12, see below) are connected to the 3-way valve such that the main force of the vacuum is isolated from the 2-way valves when the 2-way valves are closed. The vacuum valves are electrically isolated from each other via diodes.

The valves are mounted on Rainin RT96 pipet tip racks and housed in Rainin TR96 pipet tip boxes. All non-monomer connections are made with 1/16"×1/32" teflon tubing and the appropriate fittings supplied by General Valve according to their recommendations. The monomers and tetrazole lines are 0.007"ID tubing. Although tubing is desirable in that it minimizes dead volume the additional trough-filling time required by small bore tubing may be undesirable.

Motor

A Super Vexta PH268M-E1.5B 2-phase stepping motor (Inductive Components) is a suitable motor for moving the trough module.

Computer and Interface

The synthesis of DNA is controlled by computer in embodiments of the invention. Both Digital Microvax and Radio Schack TRS 80 Model 100 computers have been used with the synthesizer. Instructions from the computer control the timing and sequence of reagents which come into contact with a synthetic surface, i.e., the beads on which oligomers and synthesized, and thus determine the sequence of the oligomer synthesized on each tip. These instructions, e.g., instructions to open or close various valves (to introduce or remove a reagent from a trough), to move the trough module (to position a chosen trough under a chosen row of tips), or to raise or lower a given synthetic surface (to dip a tip into a trough), are implemented by the interface.

An Omega OM900 Series Interface (Omega Instruments, Stanford, Conn.) or similar device capable of converting instructions from the computer into signals that can control the electromechanical devices, e.g., the valves and the motor, of the synthesizer, can be used as an interface.

The Omega OM900 Series interface includes a central processing unit (OM992 Central Processing Unit), an interface power supply (OM-903 Power Supply), and a multiplex module (OM915 Multiplex Module) with 32 individually addressable relays which are used to control the valves, stepper motor, and solenoids of the device. In a device configured to synthesize DNA with six separate solenoid controlled synthetic surfaces, the 32 relays are assigned as shown in Table 1.

TABLE 1

| Relay Number | Function controlled |
|---|---|
| 1 | Oxidizer reagent (tert-butyl hydroperoxide (tBMP) delivery valve |
| 2 | Detritylation reagent (trichloroacetic acid (TCA)) delivery valve |
| 3 | Adenine ($B_z$ dA cyanoethyl phosphoramidite) delivery valve |
| 3 | Tetrazole delivery valve |
| 4 | Cytosine ($B_z$ dC cyanoethyl phosphoramidite) delivery valve |
| 4 | Tetrazole delivery valve |
| 5 | Guanine (iBu dG cyanoethyl phosphoramidite) delivery valve |
| 5 | Tetrazole delivery valve |
| 6 | Thymine (T cyanoethyl phosphoramidite) delivery valve |
| 6 | Tetrazole delivery valve |
| 7 | Oxidizer (tBHP) reagent exhaust valve |
| 8 | Detritylation (TCP) reagent exhaust valve |
| 9 | Adenine exhaust valve |
| 10 | Cytosine exhaust valve |
| 11 | Guanine exhaust valve |
| 12 | Thymine exhaust valve |
| 13 | Oxidizer rinse delivery valve |
| 14 | Detritylation rinse delivery valve |
| 15 | Adenine rinse delivery valve |
| 16 | Cytosine rinse delivery valve |
| 17 | Guanine rinse delivery valve |
| 18 | Thymine rinse delivery valve |
| 19 | Solenoid No. 1 (initial activation), 12 VDC supply |
| 20 | Solenoid No. 2 (initial activation), 12 VDC supply |
| 21 | Solenoid No. 3 (initial activation), 12 VDC supply |
| 22 | Solenoid No. 4 (initial activation), 12 VDC supply |
| 23 | Solenoid No. 5 (initial activation), 12 VDC supply |
| 24 | Solenoid No. 6 (initial activation), 12 VDC supply |
| 25 | Stepping motor (motor drive) 5 VDC supply |
| 26 | Stepping motor (motor direction) 5 VDC supply |
| 27 | Solenoid No. 1 (maintenance), 5 VDC supply |
| 28 | Solenoid No. 2 (maintenance), 5 VDC supply |
| 29 | Solenoid No. 3 (maintenance), 5 VDC supply |
| 30 | Solenoid No. 4 (maintenance), 5 VDC supply |
| 31 | Solenoid No. 5 (maintenance), 5 VDC supply |
| 32 | Solenoid No. 6 (maintenance), 5 VDC supply |

(Solenoid No. 1-6 referred to in Table 1 each control the dipping of one of the six reagent tips.)

Thus, e.g.: Relay No. 1 opens a valve which allows oxidizer to flow into the appropriate trough (trough No. 12); Relay No. 3 opens two valves, one which allows adenine monomer, and one which allows tetrazole to flow into the appropriate trough (trough No. 4); Relay No. 7 opens a valve which allows the contents to be removed from the oxidizer trough (trough No. 12); Relay No. 13 opens a valve which allows a rinsing solution to flow into the oxidizer trough (trough No. 12); Relay No. 19 controls the 12 VDC supply to solenoid No. 1 (12 VDC is required to initially activate the solenoid); Relay No. 27 controls the supply of 5 VDC to solenoid No. 1 (the voltage required to maintain the solenoid in the activated state); and Relay No. 25 and 26 which control respectively, the power to the stepping motor and the direction of the stepping motor, control the positioning of the trough module.

The assignment of a single relay to control both monomer and tetrazole valves (relays 3-6) is due to constraints imposed by the number of relays on the OM-915. Increasing the number of relays would remove the need to place more than one valve on a relay. More importantly increasing the number of relays would allow an increase in the number of solenoids, and hence in the number of simultaneous syntheses which could be performed. For example, the system could easily be expanded by the addition of six more OM-915 units. In such a configuration one OM-915 unit would be dedicated to valve and motor control and the other six OM-915 units would be dedicated to solenoid control. The use of seven OM-915 units would allow 96 controllable solenoids, and thus allow 96 simultaneous syntheses.

Figure 8:
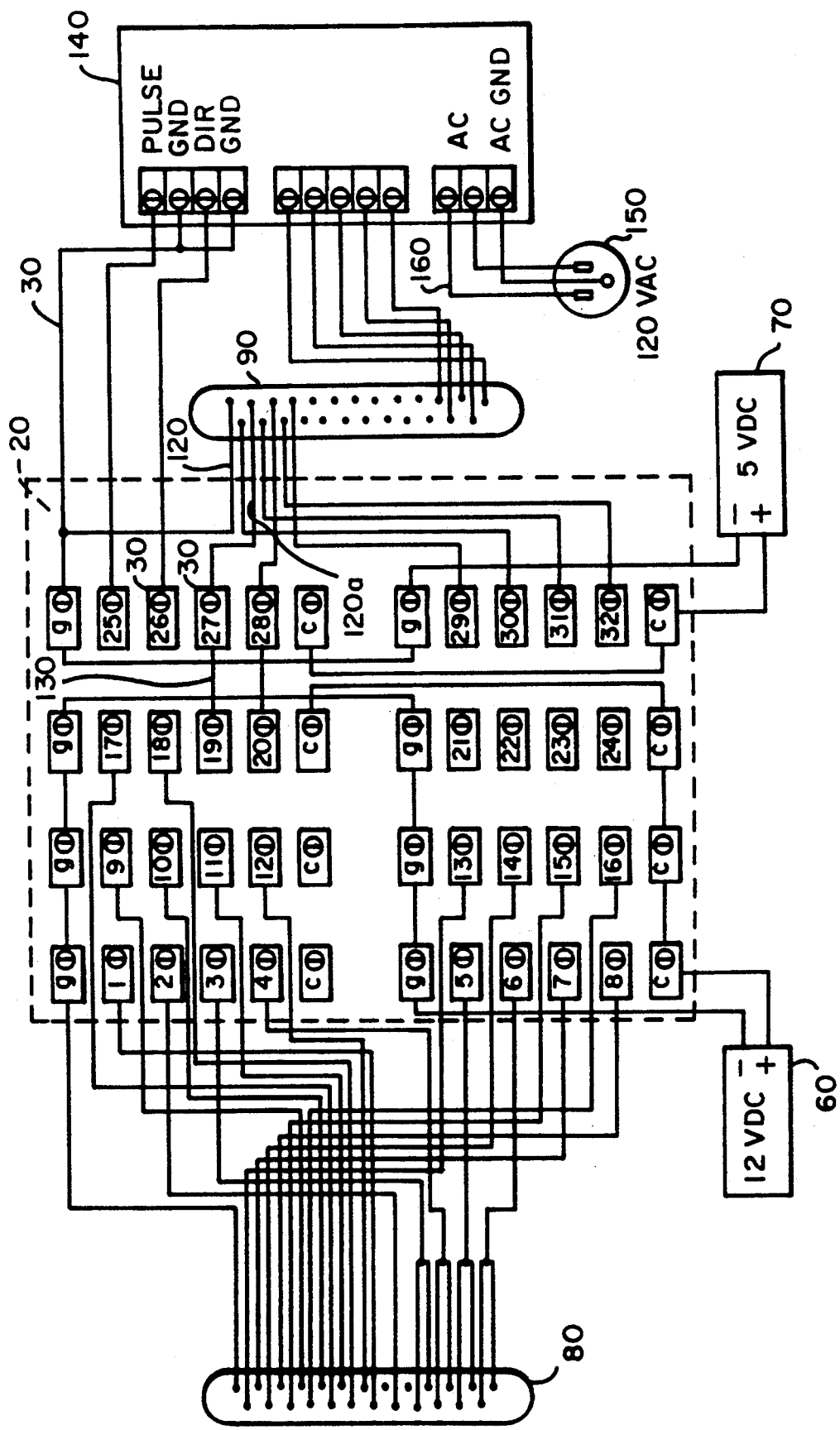
FIG. 8 is a wiring diagram of the OM-915 controller terminal board.

FIG. 8 depicts the terminal board 720 of the OM-915 interface and associated connectors. Relay terminals 730 are labeled with their relay numbers. Power is supplied to relays 730, in banks of four relays, (e.g., relay No. 1-4 constitute a bank, and relay No. 5-8, constitute a separate bank), by common contact 740 (labeled c) and ground contact 750 (labeled g). Relay No. 1-24, which control valves, are supplied with the 12 VDC from 12 DVC source 760. Relay No. 25 and 26, which control the motor, are supplied with 5 VDC from 5 VDC source 770. Relay No. 27-32, which control the activation and maintenance of the energization of the solenoids, are supplied with 12 VDC (for initial activation) from relay No. 19-24, and 5 VDC (for maintenance of activation) from the 5 VDC source 770. A SOLV 30-12 12 VDC 4A power supply (Newark Electronics), is a suitable 12 VDC source and an Elpac Model WM113+12/−12/+5 VDC power supply is a suitable 5 VDC source.

Figure 9:
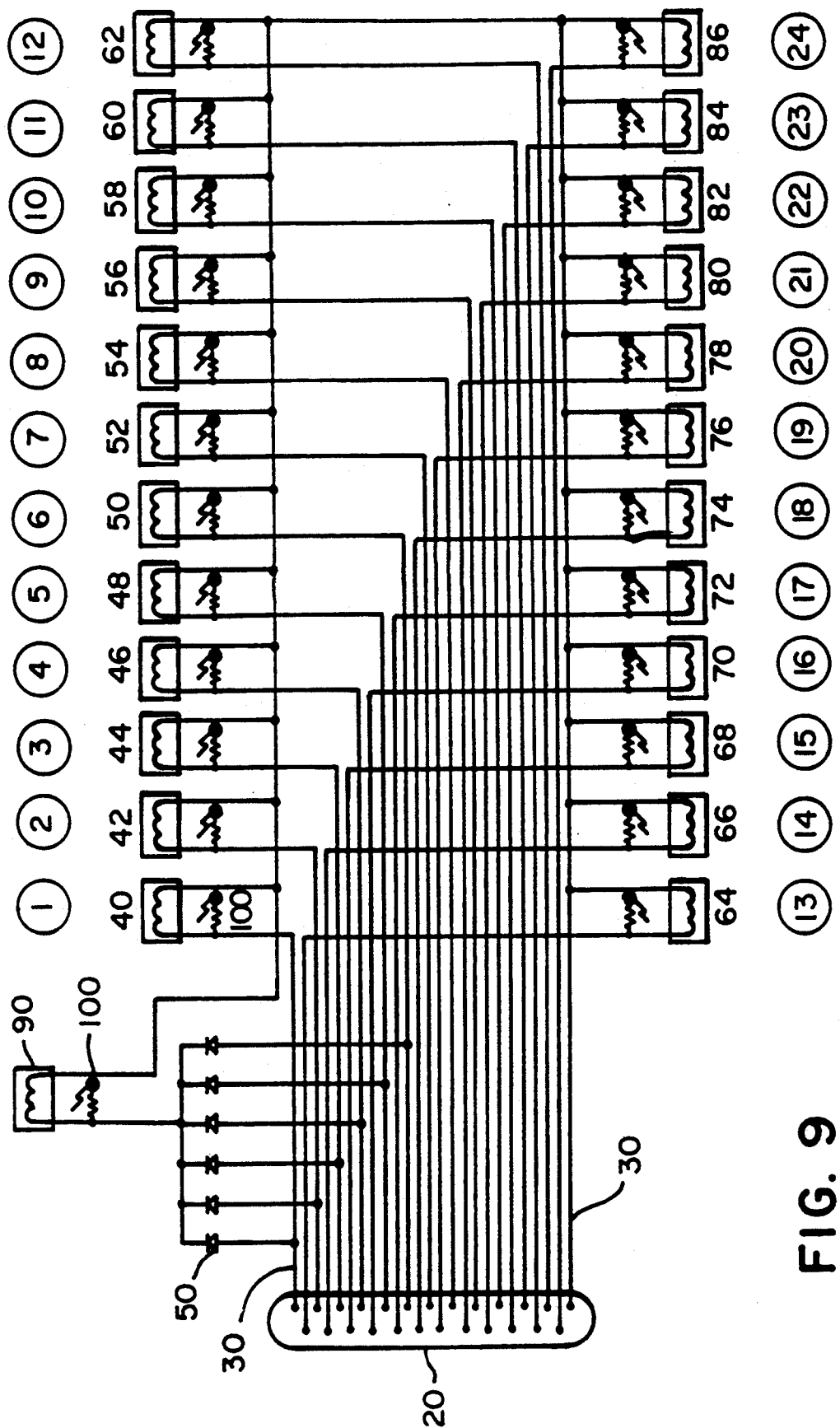
FIG. 9 is a schematic diagram of the valve block.

Relays controlling the valves are connected to controller-side valve block connector 780. As described in Table 1, Relay No. 3, 4, 5, and 6 each controls two valves. Each of these relays is thus connected to two pins on the controller-side valve block connector 780. The controller side valve block connecter 780 is connected to machine side valve block connector 920 shown in FIG. 9 which depicts the wiring of the valve block.

The machine side valve block connector 920 is connected by lines 930 to two-way valve controlling solenoids 40-86 and three-way valve controlling solenoid 990. The valve solenoids are electrically isolated by diodes 950 or light emitting diodes 1000.

Activation of any of valve controlling solenoids 940, 942, 944, 946, 948, or 950, (which are the valves controlling exhaust of a reagent from a trough), also activates 3-way valve controlling solenoid 990. For example, activation of valve controlling solenoid 940 by a signal transmitted on line 930A also activates the 3-way valve controlling solenoid 990. Thus, both the exhaust valve and vacuum control valve are opened, allowing vacuum to exhaust the trough. The circled numbers in FIG. 9 indicate the number of the 2-way valve controlled by a solenoid.

Figure 10:
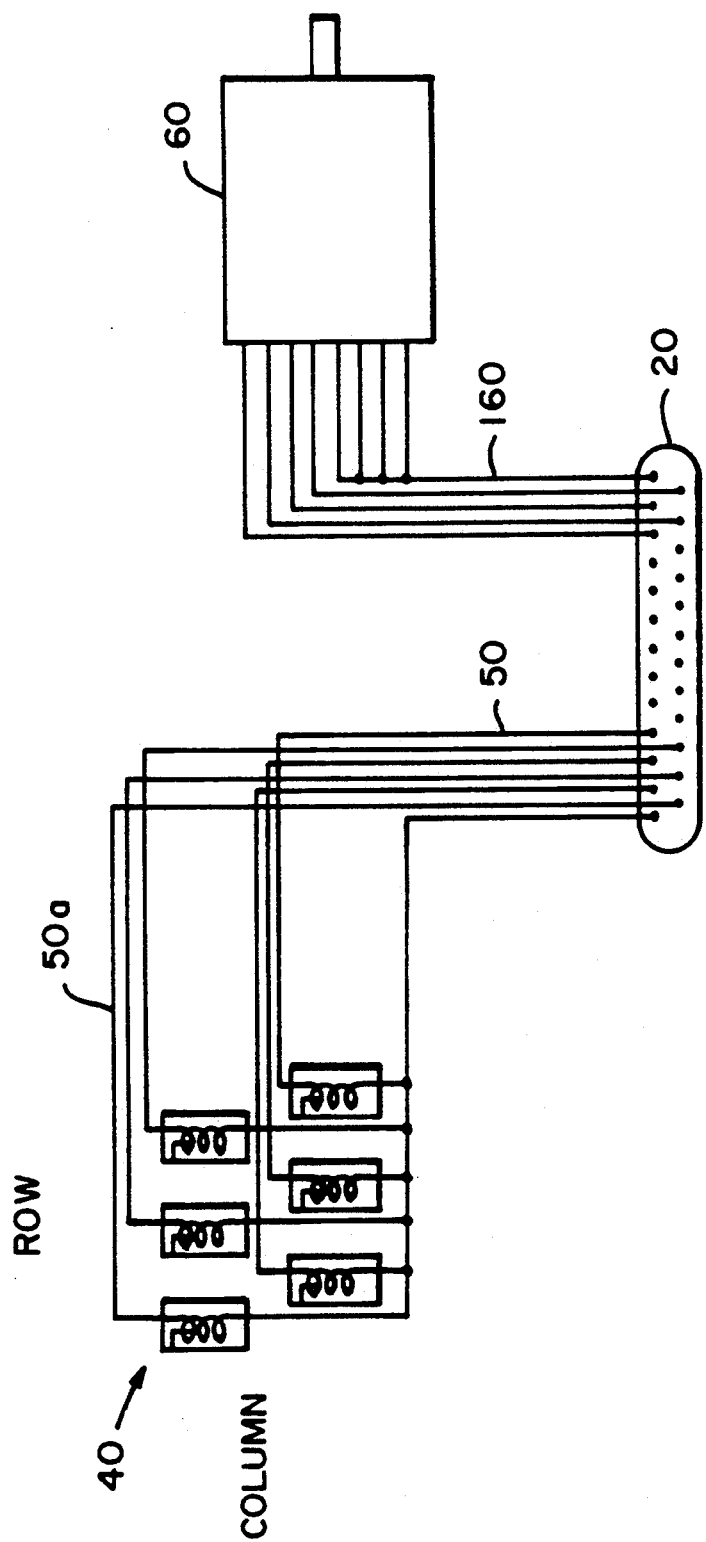
FIG. 10 is a schematic diagram of the synthesis enclosure wiring.

As shown in FIGS. 8 and 10, Relay No. 25-26, which control the stepping motor, are connected directly to the stepping motor controller by lines 810. 120 VAC source 850 is also connected to the stepping motor controller 840. Lines 860 connect the stepper motor controller, by way of controller-side enclosure connector 790, machine-side enclosure connector 1020, and lines 1160, to the stepping motor 160. Relay No. 19-24 and 27-32, which control the solenoids, are connected by lines 820 to the controller-side enclosure connector 790. The controller-side enclosure connector 790 connects to the machine side enclosure connector 1020 shown in FIG. 10. The machine side enclosure connector 1020 is connected to the solenoids 520, which are organized in a 2×3 array, by lines 1050.

With reference to Table 1, and FIGS. 8 and 10, a solenoid is activated as follows. A solenoid is lifted by 12 VDC. For example, a signal from the computer closes relay 19, which supplies 12 VDC by line 830 to relay 27 which supplies 12 VDC by line 820a to controller-side synthesis controller 790 to machine side enclosure 1020 to line 1050a and to hence to solenoid 1.

After being lifted the solenoid is maintained in the activated state by 5 VDC. The computer instructs relay 27 to close, supplying 5 VDC to solenoid 1 and opens relay 19, to remove the 12 VDC potential used to initially activate solenoid 1. At another signal from the computer, relay 27 opens and the 5 VDC potential is cut off.

Computer Software

The simultaneous synthesis of oligomers of desired sequence is directed by a computer program which controls the occurrence and relative sequence of the positioning of the trough module, the dipping of tips, and the filling and emptying of reagent troughs.

A Fortran program suitable for use with the synthesizer is included as Appendix A.

The operation of a suitable program is shown in FIG. 11. As shown in FIG. 11A the program first initializes 1120 the system. Initialization can include filling the reagent trough, dipping the tips in any trough required for activation, then bringing a designated monomer trough in position under a designated row of solenoids.

A monomer is then added 1130, the growing molecules, are capped 1140, oxidized 1150 and deprotected 1160. If there are no more additions the program ends 1170. If there are more monomers to be added 1180 the program returns to the add monomer step 1130.

The process for the addition of a monomer is described in more detail in FIG. 11B. The process for capping, oxidation, and detritylation is described in more detail in FIG. 11C.

In basic versions of the program the decision 1220 (FIG. 3B) (which tips are dipped in the addition of monomers) is asked on a row by row basis and the question of which row is dipped (for other reactions) is asked on a reaction by reaction basis. In more sophisticated versions the question is asked for the array as a whole. Thus, at the same time some tips will be dipped into the monomer trough containing A, while others are dipped into the monomer trough containing T while others are being oxidized.

The program can also include a subroutine which, e.g., upon entry of the sequences desired, determine the optimum assignment of sequences to tips and rows; determine the optimum order of the placement of reagent troughs; or control post-synthesis modification, e.g., elution or washing.

Chemistry

The chemistry of DNA synthesis is known to those skilled in the art, see e.g., Froeler et al. 1988, Nuc. Acid Res 14:5399-5407, hereby incorporated by reference. The phosphoramidite method, see Matteucci et al., 1981, J. Am. Chem. Soc. 103:3185-3191, hereby incorporated by reference and Caruthers et al., 1987, Methods Enzym. 154:287-313, hereby incorporated by reference, is suitable for use with embodiments of the invention and is described briefly below.

In the phosphoramidite method, 5' protected monomers are added to the 5' OH group on the growing molecule chain. Addition of a monomer subunit to the growing nucleotide chain requires the following steps: (1) removal of the dimethoxytrityl protecting group from the previously added (or starting) monomer with trichloroacetic acid (TCA) to form a reactive 5' hydroxyl group; (2) the addition of a 5' dimethoxytrityl protected monomer by condensation; (3) acetylation or capping of the unreactive deoxynucleoside (Step 3 is optional); and (4) oxidation of the phosphite triester to the phosphate triester with tert-butyl hydroperoxide or iodine/water. Synthesis proceeds in stepwise in a 3' to 5' direction by the sequential addition of monomers.

Operation

Oligomers are synthesized on glass beads adhered to the surfaces of the reagent tips, which can be lowered by solenoids into troughs filled with reagents. The reactions needed to add a monomer to the DNA molecules synthesized on a tip are effected by filling troughs with the appropriate reagents, e.g., a monomer, oxidizer, or rinsing agent, positioning the appropriate troughs beneath the appropriate tips in the appropriate sequence, and when an appropriate trough is positioned beneath the tip, dipping the tip into the trough. For example, addition of a monomer to a growing chain on a tip requires the following steps: (1) activating the previously added monomer by positioning the trough module such that the trough filled with detritylation reagent is below the tip, dipping the tip into the detritylation reagent to remove the dimethoxyltrityl protecting group, removing the detritylation reagent from the trough, filling the trough with a rinsing agent e.g., acetonitrile, to rinse the trough and tip, and lifting the tip; (2) adding a protected monomer by repositioning the trough module such that the trough containing the appropriate monomer is positioned below the tip, dipping the tip into the monomer trough, removing the monomer reagent from the trough, filling the trough with rinsing agent to rinse the trough and tip, and lifting the tip; (3) oxidizing the phosphite triester bond by repositioning the trough module such that the trough containing the oxidizer, e.g., tert-butyl hydroperoxide is located under the tip, dipping the tip into the oxidizer to oxidize the phosphite triester bond to a phosphate triester, removing the oxidizer and filling the trough with rinsing agent to rinse the trough and tip, and lifting the tip from the trough. This sequence of reactions results in the addition of a protected monomer to the molecules being synthesized on the tip.

In the embodiment described herein reagents, reaction times, and trough designations are as follows. Adenine monomer reagent consists of one gram of Bz dA cyanoethyl phosphoramidite in 12 ml anhydrous acetonitrile and occupies trough No. 4, thymine monomer reagent consists of one gram of T cyanoethyl phosphoramidite in 12 ml anhydrous acetonitrile and occupies trough No. 1, cytosine monomer reagent consists of oen gram of Bz dC cyanoethyl phosphoramidite in 12 ml anhydrous acetonitrile and occupies trough No. 3, and guanine monomer reagent consists of one gram of iBu dG cyanoethyl phosphoramidite in 12 ml anhydrous acetonitrile and occupies trough No. 2. Tips are exposed to monomer for three minutes then washed in acetonitrile for one minute.

Detritylation reagent consists of trichloroacetic acid in dichloromethane and occupies trough No. 8. Tips are held in the detritylation reagent for three minutes. The rinsing agent which follows detritylation consists of acetonitrile. Tips are rinsed for one minute. The oxidizing reagent consists of tert-butyl hydroperoxide 1.1M in anhydrous dichloromethane and occupies trough No. 12. Tips are held in the oxidizing reagent for one minute. After oxidation the tips and troughs are washed in acetonitrile for one minute.

Rinsing normally occurs in the same trough in which the previous reaction occurred, e.g., the post tritylation rinse occurs in trough No. 8.

At the beginning of the run, the enclosure and all lines are purged with argon and all troughs are filled with the appropriate reagents. All tips are lifted and the trough module is moved to the initiation position. The initiation position places trough 8 (TCA) beneath solenoid row 1.

Figure 12:
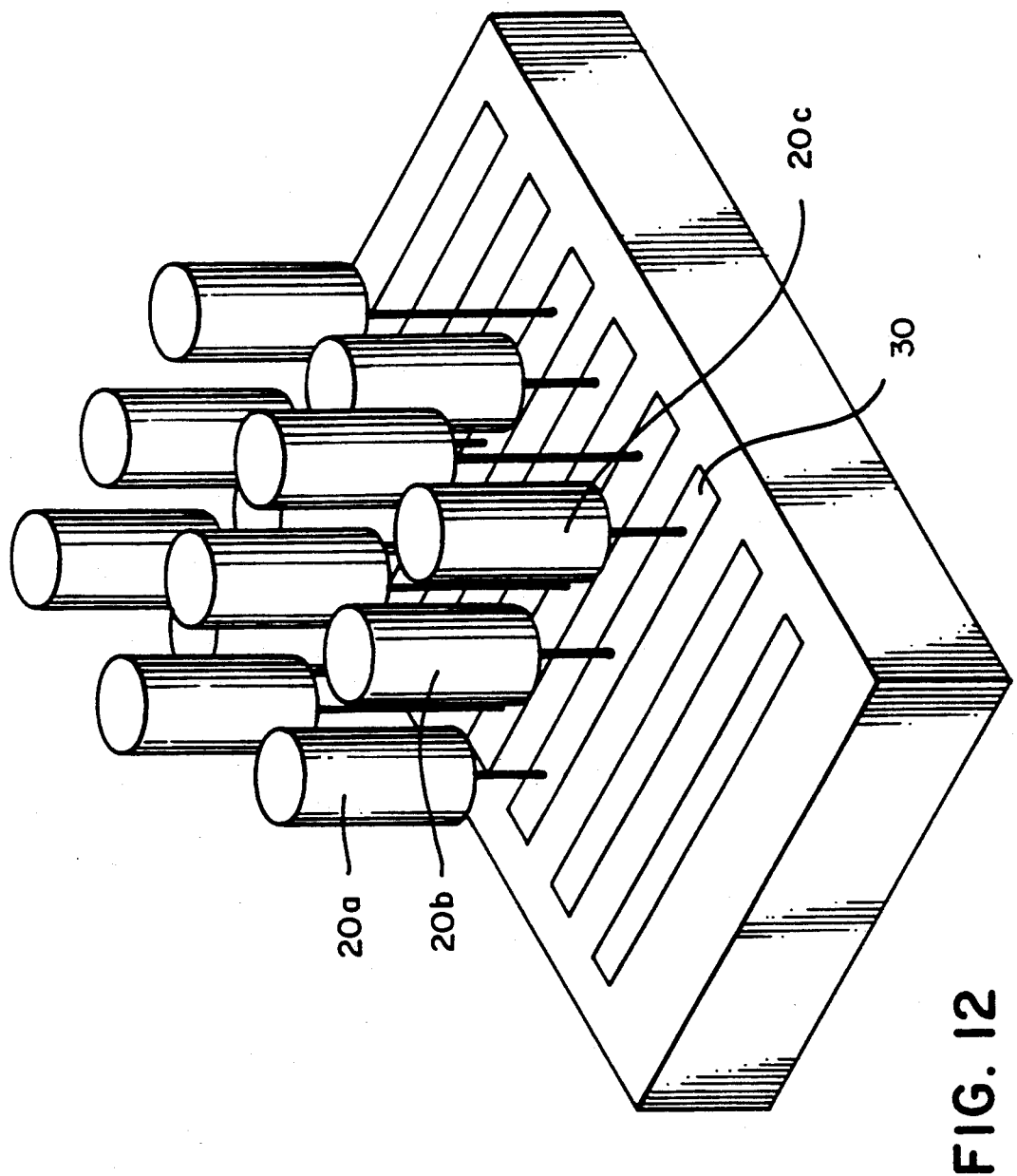
FIG. 12 is a simplified perspective diagram showing the placement of solenoid assemblies with respect to one another and with respect to the trough module.

The activation and deactivation of the solenoid (which raises and lowers a tip), the travel of the trough module (which brings a specific trough under a row of tips), and the activation of the valves which fill and empty the troughs, are all under computer control. Although, for the sake of simplicity, the action of a single tip has been described above, in actual operation, synthesis of multiple oligomers will proceed simultaneously on multiple tips. This is made possible by positioning the solenoids in an array of rows, the positioning and mobility of the troughs, the fact that each solenoid is individually addressable, the fact that multiple solenoids can be activated simultaneously, and computer control of the entire process. As shown in FIG. 12, the solenoids in a given row 520a 520b 520c are aligned such that the tips can all be dipped into the trough 170 that is positioned under that row of solenoids. When a trough is positioned under a row all of the tips in that row which require contact with the reagent in the trough positioned below that row are dipped. Tips which do not require contact with the reagent are not dipped. While tips in a row above a given trough are being dipped, the solenoids in the adjacent rows in either direction can be dipped in the corresponding adjacent troughs. Thus, synthesis of the oligomers on all tips is truly simultaneous. (To illustrate the placement of the solenoids most clearly FIG. 12 shows an embodiment with twelve solenoids and twelve reagent tips.)

The reactions can take place while a tip is actually in the reagent chamber or trough (i.e., in the reagent contact mode), or after the tip has been lifted out of the trough (i.e., in the reagent-non-contact mode), or both. For example, it may be desirable to dip tips from a plurality of rows into a trough, then to allow the reaction to proceed while some or all of the tips are out of the trough (i.e., raised). Tips treated in this way can be redipped to allow further reaction or to prevent evaporation.

Other Embodiments

Other embodiments are within the claims, e.g., the synthesizer can include an array of wells or compartments in which the completed products can be recovered or subjected to further manipulation. For example, an array of compartments, spaced such that each tip can be lowered into a single compartment, can be positioned adjacent the trough module and moved into position under the solenoid array at the completion of modification, e.g., at the completion of the synthesis of a set of DNA oligomers. The oligomers on each tip could be eluted simultaneously into the compartments. The compartments could be configured to include a filtered outlet such that the DNA eluted into each compartment could be washed and purified without transfer from the compartment. Other post synthesis manipulations could follow. Such manipulations could be performed in the same compartment or in yet another array of compartments. The standard 96 well filter plate format is particularly suitable for these embodiments in that 96 channel automatic pipette devices can be integrated into the synthesizer to serve to transfer products from one array of containers to another.

Other capacities, such as the ability to add desired reagents (e.g., cloning vectors or DNA modifying enzymes, or cells to be transformed) directly to the compartments containing the oligomers, e.g., the compartments into which the oligomers are eluted, can be added.

Embodiments of the invention allow single, or multiple reactions to take place in a single reagent trough. For example, in the synthesis of DNA oligomers, a trough used to add a monomer could contain only one monomeric species, or it could contain more than one, to allow rapid and easy synthesis of a set of probes with degeneracy at one or more positions.

Labels, e.g., chemical or radioactive labels, can be incorporated into the molecules modified. This could be achieved, e.g., by including a labeled monomer in a synthetic step or by eluting the finished products into separate containers for labeling.

Although the reagents are held statically in the reagent troughs, in some embodiments it is also possible to maintain a continuous flow of reagents in a trough.

```
Program SOLARSYNTH

Solenoid Array Synthesizer.

Print*,' Copyright (C) 1990'
Print*,' President and Fellows of Harvard College'
Print*,' Steve Kieffer-Higgins and George M. Church'
Print*,' All rights reserved'      '

Currently set up for standard CE-phosphoramidite DNA synthesis
and for Omega 992/915 RS232 interface from Omega Engineering.
To set up vax: set term/perm/eight/speed=9600 txa4
To set up Omega: connect 50-wire cable from multiplexer to relay
block.  Connect 5 VDC and 12 VDC supplies to relay block.  Connect
the 25-pin control cables to the appropriate solenoid and valve arrays.

Test with TRS-100 TELCOM stat=87I1E : 9600 baud, 7 bits, ignore
parity, 1 stop bit, line enable Modification History:

Adapted from Valve.for 2-mar-87 to SOL4S on 9-Sep-89
by George Church to SIAS_CPHOS_1 and OMEGA_CPHOS_1 on 25-jun-90
by Steve Kieffer-Higgins to SOLARSYNTH on 28-Jan-91 by Steve Kieffer-Higgins Current  setup  piston-col#1 on far right Plate-col . . . 12 11 10 9 8 7 6 5 4 3 2 1
Plate-col . . . Ox  - Cp - T - - - A G C T Piston
                col
                 2   1

Piston    8      16  8 --|
row       7      15  7   |
          6      14  6   |
          5      13  5   |__ solenoid control numbers
          4      12  4   |
          3      11  3   |
          2      10  2   |
          1       9  1 --|

Lower solenoid tier: 1,3,5,7,10,12,14,16
Upper solenoid tier: 2,4,6,8,9,11,13,15
```

For this test program only the lower tier is in use: 1,3,5,10,12,14

Valve block: Upper row, with switches to the left, are #'s 1-12, and the lower row is numbered 13-24. In this run valves 7 & 8 are not used. The monomer and tetrazole valves are currently sharing relays.

Omega relay: This run uses only one relay block consisting of 32 switches, which is currently the limiting factor for capping as well as the total possible oligos which can be made in a single run. These are the current requirements for relays assuming a two-part capping reaction:

MONOMERS: 12 RELAYS and 16 VALVES
Monomers require 1 relay to simultaneously switch of 2 valves, monomer and tetrazole. Each also requires a dedicated rinse and vacuum valves. Thus, each monomer requires 4 valves controlled by 3 relays for a total of 16 valves and 12 relays.

OXIDATION: 3 RELAYS and 3 VALVES
The oxidizer is a one part reagent which requires dedicated rinse and vacuum valves.

CAPPING: 3 RELAYS and 4 VALVES
The capping reagent is a two-part mixture which requires dedicated rinse and vacuum valves.

TCA: 3 RELAYS and 3 VALVES
TCA is a one part reagent which requires dedicated rinse and vacuum valves.

MOTOR: 4 RELAYS
The motor requires 2 relays at 5VDC. Since the relay blocks can switch different voltages in groups of 4 and the valves all require 12VDC, the motor effectively takes 4 relays out of the pool.

TOTAL: 29 RELAYS and 26 VALVES for reagent delivery and trough moveme

SOLENOIDS: 2 RELAYS EACH
The solenoids require 12VDC to pull up a tip and switching to 5VDC to maintain a hold on the tip. The solenoids reach a temperature greater than 100C when in an array with continuous application of 12VDC, but reach about 35C at 5VDC. Thus each Omega OM915 relay module can control 16 individual solenoids, or a total of 6 OM915 units for 96 solenoids.

The present set up with a single OM915 allows the control of 6 solenoids if we work without a capping reaction. Not capping saves 3 relays and 4 valves. Based on the architecture of the relay blocks, which allows voltages in groups of 4 to be switched, we would be reduced to only 3 different oligos per run were we to incorporate a capping reaction.

RELAY/VALVE ASSIGNMENTS:

| OMEGA RELAY | REAGENT | VALVE |
|---|---|---|
| 1 | tBHP | 19 |
| 2 | TCA | 20 |
| 3 | A monomer | 21 |
|   | TET-A | 9 |
| 4 | C monomer | 22 |
|   | TET-C | 10 |
| 5 | G monomer | 23 |
|   | TET-G | 11 |
| 6 | T monomer | 24 |
|   | TET-T | 12 |
| 7 | vac-tBHP | 1 |
| 8 | vac-TCA | 2 |
| 9 | vac-A | 3 |
| 10 | vac-C | 4 |
| 11 | vac-G | 5 |
| 12 | vac-T | 6 |
| 13 | CH3CN-tBHP | 13 |
| 14 | CH3CN-TCA | 14 |
| 15 | CH3CN-A | 15 |
| 16 | CH3CN-C | 16 |

| | | |
|---|---|---|
| 17 | CH3CN-G | 17 |
| 18 | CH3CN-T | 18 |
| 25 | Motor - Drive | 25 |
| 26 | Motor - CW/CCW | 26 |
| 19-24 | 12V solenoids | |
| 27-32 | 5V solenoids | |

Each step entails a CH3CN rinse that rinses both the reagent troughs and the tips used in that trough during that step. In this way no additional valves/relays are required to effect a rinse. Additionally, the same control loop can be used for both the chemical and rinse steps with only an update in the control variables. This feature will be most useful in preventing cross-contamination of adjascent tips in the first rinses after monomer addition.

Manual synthesis cycle as performed SKH 14-Jun-90

```
          Pos
       1. CH3CN         20"
       2. TCA           5 x 10"
          CH3CN         20"
       3. Base          180"
          CH3CN         20"
       4. Cap           120"
          CH3CN         20"
       5. Oxid          60"
          CH3CN         20"
```

```
integer*4      lenmax ! maximum length of oligos to be made integer*4      colmax ! maximum number of columns - hardware dependant integer*4      rowmax ! maximum number of row - hardware dependant integer*4      stepmax ! number of synthetic steps + 1 (initiation)

integer*4      troughmax ! number of reagent troughs, currently 6
               BUT must be incremented to 7 when capping is added.

integer*4      trough_unit ! the number of motor steps to move 9mm integer*4      rxnstep ! the number of substeps per synthetic step.
               Currently 3: the actual reaction, vacuuming out the
               trough, and adding rinse.

integer*4      vlvmax! The number of commands that must be sent to
               a given trough, currently 6: open/close reagent,
               vacuum and rinse.

parameter( lenmax=38, colmax=2, rowmax=3, stepmax=5)
parameter( troughmax=6, trough_unit=33, rxnstep=3, vlvmax=6)

real*4         pos(stepmax) !The absolute position of a reagent
               trough within the trough plate - defined by user
               in SOLARSYNTH.TMR real*4         pumptm(stepmax,rxnstep)!The length of time to hold
               a valve open - defined by user in SOLARSYNTH.TMR real*4         wait(stepmax)!Reaction time per step - defined by
               user in SOLARSYNTH.TMR real*4         wait2(stepmax)!Rinse time per step - defined by
               user in SOLARSYNTH.TMR logical        long !toggles between full length reaction steps.
               When TRUE the times defined in SOLARSYNTH.TMR are
               converted from minutes to seconds; otherwise the
               minutes are treated as seconds.

logical        yescheck ! required by GETSTR integer*4      ldrvcmand, lcmand, lreset, lcpureset ! Length of
               command strings sent to WRIBOT
```

| | |
|---|---|
| integer*4 | step ! Control variable which keeps track of where in the synthesis cycle the program is. |
| integer*4 | loopbeg, loopend ! the bounds in which STEP operates |
| integer*4 | mono ! the number of monomers, currently 4 |
| integer*4 | NC, NR ! the actual number of columns and rows of oligos to be made which will vary with each run |
| integer*4 | len ! the length of the longest oligo to be made per run |
| integer*4 | cyc ! control variable which operates within the bounds of LEN, above |
| integer*4 | ld(colmax,rowmax), lu(colmax,rowmax)! length of commands that raise (lu) and lower (ld) the solenoids, required by WRIBOT |
| integer*4 | seqm(colmax,rowmax,lenmax)!integer representation of the oligos to be made, where A=1, C=2 etc |
| character*1 | mlis(20) ! reference against which an element of SEQM above is compared when the program is testing to see if a solenoid is to drop its tip. When the number in the SEQM array matches the subscript of MLIS, the tip is dropped. |
| character*30 | Chem(stepmax), chem2(stepmax) !Description of each step: Chem=rxn, chem2=rinse |
| character*38 | seq(colmax,rowmax) |
| character*60 | drive(3) !Holds the commands that drive the motor: 1= pulse, 2=CW, 3=CCW |
| character*60 | check !dummy var required for GETSTR |
| character*60 | rxnvlv(troughmax, vlvmax)!holds the open and close commands for the valves |
| character*60 | cpureset,reset !Reset commands for Omega CPU and OM915 |
| character*60 | down(colmax,rowmax), up(colmax,rowmax)! Lift and drop commands for the solenoids |

```
****************************************************************
MAINLINE call INITIALIZE( chem, chem2, colmax,
2       cpureset, down, drive, lcpureset, ld, ldrvcmand,
3       len, lenmax, long, loopbeg, loopend, lreset, lcmmnd,
4       lu, mlis, mono, pumptm, rxnstep,
5       NC, NR, pos, reset, rowmax, rxnvlv, seq, seqm,
6       stepmax, trough_unit, troughmax, up, vlvmax, wait, wait2)

call getstr(check,'Hit RETURN to begin synthesis.','<CR>',yescheck)

Do cyc=2,Len
   Do step = loopbeg, loopend if (step.eq.2) then
         call ADD_MONOMER (chem, chem2,
2        colmax,cyc,down,drive,ld,lenmax,ldrvcmand, lcmmnd,
3        lu, mlis, mono, NC, NR, pos, pumptm, rxnstep,
4        rowmax, rxnvlv, seqm, step, stepmax,
5        trough_unit, troughmax, up, vlvmax, wait, wait2)

else
         call NON_ADDITIVE_CHEMISTRY(chem, chem2,
2        colmax, down, drive, long, ld,
3        ldrvcmand, lcmmnd, lu, rxnstep,
```

```
4          NC, pos, pumptm, rowmax, rxnvlv, step,
5          stepmax,troughmax,trough_unit, up,vlvmax, wait, wait2)

end if
   End do ! step

End do ! cyc call wribot( reset(1:lreset) )

END !solarsynth

*****************************************************************
subroutine NON_ADDITIVE_CHEMISTRY(chem, chem2,
2         colmax, down, drive, long, ld,
3         ldrvcmmnd, lcmmnd, lu, rxnstep,
4         NC, pos, pumptm, rowmax, rxnvlv, step,
5         stepmax, troughmax, trough_unit, up, vlvmax, wait, wait2)

coordinates TCA, oxidation and capping steps integer*4      colmax,rowmax,stepmax,troughmax,rxnstep,vlvmax real           time, delta, oldpos
real*4         pos(stepmax), pumptm(stepmax, rxnstep)
real*4         wait(stepmax), wait2(stepmax)
logical        long
integer*4      NC, vlv, i, step, trough_unit
integer*4      ldrvcmmnd, lcmmnd
integer*4      ld(colmax,rowmax), lu(colmax,rowmax)
character*30   Chem(stepmax), chem2(stepmax)
character*60   drive(3)
character*60   down(colmax,rowmax), up(colmax,rowmax)
character*60   rxnvlv(troughmax, vlvmax)

if (step.eq.3) return !cap
if (step.eq.4) then
        vlv=1  !oxidize
        oldpos=5
end if
if (step.eq.5) then
        vlv=2  !TCA
        oldpos=12
end if call MOVEx (oldpos,pos(step), drive, ldrvcmmnd,
2                       lcmmnd, trough_unit)

fill trough: reagent valve = 1
call pump(rxnvlv(vlv,1), rxnvlv(vlv,2),lcmmnd,pumptm(step,1))

react tips:

print*,chem(step)
write(66,'(a)')chem(step)
delta=0
time=secnds(0.0)
print*,'REACTION TIME=',(wait(step)/60),'minutes'
write(66,'(a,f,a)')'REACTION TIME=',(wait(step)/60),'minutes'
do while(delta.lt.wait(step))
    delta=secnds(time)
    call dip_all_cols(colmax, down, drive, ld, ldrvcmmnd,lcmmnd,
2         lu, NC,pos, rowmax, step, stepmax, trough_unit, up)
end do! while rinse trough print*,chem2(step)
write(66,'(a)')chem2(step)
delta=0
time=secnds(0.0)
print*,'RINSE TIME=',(wait2(step)/60),'minutes'
write(66,'(a,f,a)')'RINSE TIME=',(wait2(step)/60),'minutes'
```

```
        call pump(rxnvlv(vlv,3), rxnvlv(vlv,4), lcmmnd, pumptm(step,3))
        do while (delta.lt.wait2(step))

remove reagent:

rinse:
            print*,chem2(step)
            write(66,'(a)')chem2(step)
            call pump(rxnvlv(vlv,5), rxnvlv(vlv,6), lcmmnd, pumptm(step,2))

do i = 1, 5
                call dip_all_cols(colmax, down, drive, ld, ldrvcmmnd,lcmmnd,
     2              lu, NC, pos, rowmax, step, stepmax, trough_unit, up)

end do !dip
            call pump(rxnvlv(vlv,3), rxnvlv(vlv,4), lcmmnd, pumptm(step,3))
            delta=secnds(time)

end do !while return end ! non_additive _chemistry

********************************************************************
        subroutine INITIALIZE( chem, chem2, colmax,
     2      cpureset, down, drive, lcpureset, ld, ldrvcmmnd,
     3      len, lenmax, long, loopbeg, loopend, lreset, lcmmnd,
     4      lu, alis, mono, pumptm, rxnstep,
     5      NC, NR, pos, reset, rowmax, rxnvlv, seq, seqm,
     6      stepmax, trough_unit, troughmax, up, vlvmax, wait, wait2)

integer*4       col,row,colmax,rowmax,stepmax,rxnstep,vlvmax
        real*4          pos(stepmax), pumptm(stepmax, rxnstep)
        real*4          wait(stepmax), wait2(stepmax)
        logical         long, yescheck
        integer*4       troughmax, loopbeg, loopend,stepnum
        integer*4       i, b, bb, q, p, m, mono, trough_unit
        integer*4       Len, lenmax, seqm(colmax,rowmax,lenmax)
        integer*4       NC, NR, vlv, ldrvcmmnd, lcmmnd, prm
        integer*4       ld(colmax,rowmax), lu(colmax,rowmax)
        integer*4       lreset, lcpureset, rotn
        character*1     alis(20), newdir, oldir
        character*8     waitasec
        character*30    Chem(stepmax), chem2(stepmax)
        character*38    seq(colmax,rowmax)
        character*60    dummyline
        character*60    cpureset, reset, halt, CW, CCW
        character*60    down(colmax,rowmax), up(colmax,rowmax)
        character*60    drive(3), str, check, prmvlv, vacprm
        character*60    rxnvlv(troughmax,vlvmax)

Colmax & rowmax determine the number of pins used in the program.
        With only one OM-915 we have room for only 6 individually
        adressable solenoids, 2 columns x 3 rows. Stepmax = 6, which
        reflects the initial step of starting the synthesis and 4
        synthetic reactions: 2=monomer addition, 3=cap ( not used
        in this version), 4=oxidation, 5=trityl release. Each step
        has a CH3CN rinse at the end.

Loopbeg= 2   ! Start with preloaded detritylated solid phase
        Loopend= 5   ! 4 actual synthesis steps, if we use capping Solenoid columns begin with one on the left.
        At X=0.0 , pos=1 lines up with col=1, pos=2 with col=2 etc.

mono = 4 ! number of monomer solutions 4 = ACGT
        call getstr(str,' Long(full) version or rapid check','rapid',long)
        long=.not.long alis(1)='A'
        alis(2)='C'
```

```
alis(3)='G'
alis(4)='T'

Chem( 1)= 'M Start'
pos( 1)= 8  ! trough is moved to monomer pos from TCA pos
```

The following routines establish the timing parameters for each step. The user may input any timing parameter as minutes in real numbers, ie 3.5 instead of 3:30. Input file follows this format:

filename: SOLARSYNTH.TMR

```
line#   content
1.      MINUTES[TAB]TROUGH POS[TAB]TROUGH FILLING TIME

2.      MONOMER COUPLING
3.      rxn time [spaces] trough pos [spaces] time to fill trough
4.      MONOMER RINSE
5.      rinse time [spaces] time to fill trough
6.      MONOMER TROUGH VACUUM
7.      time to empty trough.

8.      CAPPING REACTION
9.      rxn time [spaces] trough pos [spaces] time to fill trough
10.     CAPPING RINSE
11.     rinse time [spaces] time to fill trough
12.     CAPPING TROUGH VACUUM
13.     time to empty trough
14.     OXIDATION
15.     rxn time [spaces] trough pos [spaces] time to fill trough
16.     OXIDATION RINSE
17.     rinse time [spaces] time to fill trough
18.     OXIDATION TROUGH VACUUM
19.     time to empty trough 20.     TCA TRITYL RELEASE
21.     rxn time [spaces] trough pos [spaces] time to fill trough
22.     TCA RINSE
23.     rinse time [spaces] time to fill trough
24.     TCA TROUGH VACUUM
25.     time to empty trough print*,'Opening SOLARSYNTH.TMR for timing parameters...'
open(11,name='solarsynth.tmr',status='old',readonly)

take care of header:
read(11,'(a)')dummyline
read the 4 sets of timing parameters:
do i= 2, 5
        read(11,'(a)')chem(i)
write(66,*)'chem(i)',chem(i)
        read(11,*)wait(i),pos(i),pumptm(i,1)
write(66,*)'wait(i),pos(i),pumptm(i,1)',wait(i),pos(i),pumptm(i,1)
        read(11,'(a)')chem2(i)
        write(66,*)'chem2(i)',chem2(i)
        read(11,*)wait2(i),pumptm(i,2)
write(66,*)'wait2(i),pumptm(i,2)',wait2(i),pumptm(i,2)
        read(11,'(a)')dummyline
        read(11,*)pumptm(i,3)
write(66,*)'pumptm(i,3)',pumptm(i,3)
end do !i
if (long) then
    do i=2,5
        wait(i)=wait(i)*60
        wait2(i)=wait2(i)*60
    end do
end if read sequence data:
print*,'Opening SEQUENCE.IN for synthesis parameters...'
Open(10,name='sequence.in',status='old',readonly)
Len=0
Do col=1,colmax
    Do row = 1, rowmax
        read(10,'(a)',err=9,end=9)seq(col,row)
```

```
      determine Len, flip 3' to 5', and translate to monomer #
      do b=1,lenmax
         seqm(col,row,b)=0 ! initialize to no monomer coupling
      end do
      bb=0
      do b=lenmax,1,-1
         do m=1,mono
            Check Upper and lowercase ACGT,etc.:
            If( char(ichar(seq(col,row)(b:b))-32).eq.mlis(m)
     &         .or.seq(col,row)(b:b).eq.mlis(m) ) then
               bb=bb+1
               if(bb.eq.1) write(66,*)'_'
               seqm(col,row,bb)=m
               writes a #:1,2,3 or 4,corresponding to a monomer
               write(66,'(a,4i4,x,a)')' Col,Row,base,m'
     &            ,col,row,bb,m,seq(col,row)(b:b)
               goto 1
      End do print*,'CPU RESET'
      write(66,'(a)')'CPU RESET'
      call wribot(cpureset (1:lcpureset))

print*,'MULTIPLEXER RESET'
      write(66,'(a)')'MULTIPLEXER RESET'
      call wribot(reset (1:lreset))

NC=col-1
      NR=row-1
      If(NR.le.0) then
         NR=rowmax
         NC=NC-1
      End If

*     Initialize all relays to the no power state, then set to "UP".
      Do col = 1,NC
         Do row = 1,rowmax
            If(col.eq.NC.and.row.gt.NR) goto 2
            call wribot( up(col,row)(1:lu(col,row)) )
         End do ! row
      End do ! col 2     continue
      print*,'Enter the number which corresponds to desired operation:'
      print*,' '
      print*,'1. Position trough unit.'
      print*,'2. Prime reagents.'
      print*,'3. Activate solenoids.'
      print*,'4. Initiate synthesis.'
      print*,' '
      call getlint(prm,'Your choice?',999)
      if (prm.eq.999) goto 2
      if (prm.lt.1) goto 2
      if (prm.gt.4) goto 2 if (prm.eq.1) call position_trough(drive,lcmmnd,ldrvcmmnd,
     2      trough_unit)

if (prm.eq.2) call prime_reagents(cpureset,lcmmnd,lcpureset,
     2      lreset,reset)

if (prm.eq.3) call solenoids(colmax,down,ld,lu,NC,rowmax,up)

if (prm.eq.4) goto 3 goto 2

3     continue return end !initialize

************************************************************************
      subroutine DIP_ALL_COLS (colmax, down, drive, ld, ldrvcmmnd,lcmmnd,
     2      lu, NC, pos, rowmax, step, stepmax, trough_unit, up )
```

* Dips all tips one column at a time into a given trough

```
        integer*4       col, row, rowmax, stepmax, colmax
        real*4          pos(stepmax), newpos
        integer*4       NC, NR, step, trough_unit, ldrvcmnd, lcmnd
        integer*4       ld(colmax,rowmax), lu(colmax,rowmax), i,q
        character*8     waitasec
        character*60    down(colmax,rowmax), up(colmax,rowmax), drive(3)

waitasec='0:00.50'
        Do col = 1,NC
          do i=1, 5
            Do row = 1,rowmax
                If(col.eq.NC+1.and.row.gt.NR) goto 4
                Call wribot(down(col,row)(1:ld(col,row)) )
            end do !-row call waiter(waitasec)

do q=1,5
            Do row = 1,rowmax
                Call wribot(up(col,row)(1:lu(col,row)) )
            end do ! row
          end do !q
          newpos=pos(step)-col
          end do ! i if (col.lt.NC) call movex
     2       (pos(step)-col+1,newpos,drive,ldrvcmnd,lcmnd,trough_unit)
          if (col.eq.NC) call movex
     2       (pos(step)-col+1,pos(step),drive,ldrvcmnd,lcmnd,trough_unit)
    4   End do ! col
        continue
        return end ! dip_all_cols

*****************************************************************
        subroutine ADD_MONOMER (chem, chem2,
     2      colmax,cyc,down,drive,ld,lenmax,ldrvcmnd, lcmnd,
     3      lu, alis, mono, NC, NR, pos, pumptm, rxnstep,
     4      rowmax, rxnvlv, seqm, step, stepmax,
     5      trough_unit, troughmax, up, vlvmax, wait, wait2)

*   Coordinates monomer addition integer*4       colmax,rowmax,stepmax,lenmax,rxnstep,vlvmax
        real            delta, time
        real*4          pos(stepmax),pumptm(stepmax,rxnstep)
        real*4          wait(stepmax), wait2(stepmax)
        logical         long
        integer*4       ldrvcmnd, lcmnd, step, mono, cyc, q
        integer*4       NC, NR, co, i, troughmax, trough_unit
        integer*4       ld(colmax,rowmax), lu(colmax,rowmax)
        integer*4       seqm(colmax,rowmax,lenmax),firstmono,lastmono
        character*1     alis(20)
        character*30    chem(stepmax), chem2(stepmax)
        character*60    drive(3)
        character*60    rxnvlv(troughmax, vlvmax)
        character*60    down(colmax,rowmax), up(colmax,rowmax)

*  pump monomers:
        firstmono = 3  !INCREASE TO 4 WITH CAPPING
        lastmono  = 6  !INCREASE TO 7 WITH CAPPING do i=firstmono, lastmono
            call pump(rxnvlv(i,1), rxnvlv(i,2),lcmnd,pumptm(step,1))
        end do

*   while there is time: wait
        call movex(pos(step-1),pos(step),drive,ldrvcmnd,lcmnd,trough_unit)
        print*,chem(step)
*       write(66,*)chem(step)
        delta=0
```

```
      time=secnds(0.0)
      do while (delta.le.wait(step))
          call addition  (cyc, colmax, down, drive, ld,ldrvcmmnd,lcmmnd,
     2        lenmax,lu,mlis,mono, NC, NR,, pos, rowmax, seqm, step,
     3        stepmax, troughmax, trough_unit, up)

delta=secnds(time)
      end do! addititon

*     while there is time : wait2
      print*,chem2(step)
      write(66,*)chem2(step)
      delta=0
      time=secnds(0.0)

*     remove reagent:
      do i= firstmono, lastmono
          call pump(rxnvlv(i,3), rxnvlv(i,4), lcmmnd, pumptm(step,3))
      end do do while (delta.le.wait2(step))
*     pump rinse:
          do i= firstmono, lastmono
              call pump(rxnvlv(i,5), rxnvlv(i,6), lcmmnd, pumptm(step,2))
          end do do q=1, 5
              call addition (cyc,colmax,down,drive,ld,ldrvcmmnd,lcmmnd,
     2            lenmax,lu,mlis,mono, NC, NR, pos, rowmax, seqm, step,
     3            stepmax, troughmax, trough_unit, up)
          end do ! q
          delta=secnds(time)
          do i= firstmono, lastmono
              call pump(rxnvlv(i,3), rxnvlv(i,4), lcmmnd, pumptm(step,3))
          end do end do! rinse return end ! add monomer

**************************************************************************
      subroutine ADDITION  (cyc,colmax,down, drive,ld,ldrvcmmnd,lcmmnd,
     2        lenmax,lu,mlis,mono,NC, NR, pos, rowmax,seqm,step,stepmax,
     3        troughmax, trough_unit, up)

*     decides which tips drop into which monomer trough integer*4       col, row, colmax, rowmax, stepmax, lenmax
      real*4          pos(stepmax), lastep, firstep
      logical         long, drop
      integer*4       b, bb, cyc, dip, loopbeg, loopend, m,mono,step
      integer*4       NC, NR, co, i, c, r, trough_unit, troughmax,q
      integer*4       ld(colmax,rowmax), lu(colmax,rowmax),  lcmmnd
      integer*4       seqm(colmax,rowmax,lenmax),ldrvcmmnd
      character*1     mlis(20)
      character*8     waitsec
      character*60    down(colmax,rowmax), up(colmax,rowmax), drive(3)

waitsec='00:01.00'
      firstep = pos(step)
              End If
          End do ! m
        End do ! b
    1 If( Len.lt.bb) Len=bb
        End do ! row
      End do ! col
      col=colmax ! on leave fortran loop index goes +1 beyond limit!
    9 continue

*     interface resets:

write(cpureset,'(a)')'@RESET'//char(13)//char(10)
      write(reset,'(a)')'#1 RESET'//char(13)//char(10)
      lcpureset=8
      lreset=10
```

```
*       valve assignments:
*       We are currently set up for 6 reagent troughs, each with dedicated
*       reagent, vacuum & rinse valves.  Capping is not used.  If we add
*       capping later the omega relay block will have to be rewired to
*       reflect this and the control var TROUGHMAX should be increased to 7.
*       The variable q reflects the actual Omega relay number.  Once capping
*       has been integrated into the program the wiring harness must be
*       rewired so that relay 1=tBHP, 2=CAP, 3=TCA, 4=A monomer, etc.

q=1
        do p=1,vlvmax,2
            do i=1, troughmax
                write(rxnvlv(i,p),'(a,i2,a)')'#1,SW',q,'=1'
     2              //char(13)//char(10)
                write(rxnvlv(i,p+1),'(a,i2,a)')'#1,SW',q,'=0'
     2              //char(13)//char(10)
                q=q+1
            end do ! vlvmax
        end do ! troughmax

*       relays 19 - 24 = solenoid 12V

MOTOR - drive req 5V
        write(drive(1),'(a)')'#1,SW25=1;SW25=0'//char(13)//char(10)

*       MOTOR - CW/CCW
        write( drive(2) ,'(a)')'#1,SW26=1'//char(13)//char(10)
        write( drive(3),'(a)')'#1,SW26=0'//char(13)//char(10)

ldrvcmmnd = 19
        lcmmnd = 11

*       relays 27-32 = solenoid 5V

*       lift & drop commands for the solenoids:

m=18 !1st 12V solenoid assignment on OM-915 is next, 19
        Do col=1,colmax ! col = x
            Do row=1,rowmax ! row = y
                ld(col,row)=11 ! 11 characters long
                lu(col,row)=25 ! 25
                m=m+1
                write(down(col,row),'(a,i2,a)')'#1,SW',m+8,'=0'
     2              //char(13)//char(10)
*               print*,'COL, ROW, DOWN(col,row)',col ,row, down(col,row)
                write( up(col,row),'(a,i2,a,i2,a,i2,a)')
     2              '#1,SW',m,',',m+8,'=1'//char(13)//char(10)//
     3              '#1,SW',m,'=0'//char(13)//char(10)
*               print*,'COL, ROW, UP(col,row)',col ,row, up(col,row)
            End do
        lastep = pos(step)
        drop=.false. !conditional for monomer dip
!       NC holds same value as COLMAX:
        Do col = 1, NC+3
            call MOVEx( lastep, firstep-col+1, drive,ldrvcmmnd,
     2              lcmmnd, trough_unit)

!           pos(step) for monomers= -3, such that the first
!           column of tips stands directly above the 'A' trough.
!           When col=2, move is to position -2, etc.

Do row = 1,rowmax
!           bailout conditional:
        If(col.eq.NC+3.and.row.gt.NR) goto 7
!           then the last column/row is past the end !           min(mono,col) returns the smallest #, mono, which = 4,
!           or col, which increments by 1 from 1 to NC+3
!           first pass: m=1; loop is used once:only one column
!           could be over the first monomer trough.
!           Second pass, m=2; loop used twice, 2 columns are
!           over monomer troughs:
            Do m=min(mono,col),1,-1
                co=col-m+1       ! first pass: co=1-1+1 = 1
                if(co.gt.NC) goto 11
                if(co.eq.NC.and.row.gt.NR) goto 11    !bailout conditional
```

```
!                       test to see if the integer held in seqm(co,row,cyc),
!                       which corresponds to a monomer, is the same as m
!                       first pass: m=1

If(seqm(co,row,cyc).eq.m) then
!                          if it does write to output file & drop that tip:
                           write(66,'(a,4i3,x,a)')' Cyc,col,row,co, base',
      2                       cyc,col,row,co, mlis(m)
                           call wribot( down(co,row)(1:ld(co,row)) )
                        end if !
                     end do !m
11                   continue
                  end do ! row
                  call waiter(waitsec)

!                 lift tips:cmnd to all
                  do c=1,NC
                     do r=1,rowmax
                        if (c.eq.NC.and.r.gt.NR) goto 14
                        do q=1,5
                           call wribot( up(c,r)(1:lu(c,r)) )
                        end do ! q
                     end do !row
                  end do ! col 14             continue
               lastep=firstep-col+1
               drop=.false.

End do ! col
7        Continue
         call MOVEx(lastep-1,firstep,drive,ldrvcmnd,lcmnd,trough_unit)

return

End ! addition
!*****************************************************************
         subroutine wribot(data)
!
!        To output strings of unknown length to serial RS232 port
!        without terminal <CR> or other characters.
!        Version 1.0     Apr 2 1987        GMC
!
         integer*2       ttchan,ttinit,iosb(4)
         integer*4       i,SYS$QIOW,icode,funcw,efn
         integer*4       LIB$GET_EF,LIB$FREE_EF
         character*(*)   data include '($iodef)'
         external IO$_WRITEVBLK,IO$M_NOFORMAT ttchan=ttinit()
         funcw=ior(%loc(IO$_WRITEVBLK),%loc(IO$M_NOFORMAT))
         icode=LIB$GET_EF(efn)
         if (.not.icode) call LIB$SIGNAL(%VAL(icode))
         icode = SYS$QIOW ( %val(efn),%val(ttchan),%val(
      2     funcw),iosb,,,%ref(data),%val(len(data)),,%val(0),, )
         if (.not.icode) call LIB$SIGNAL(%VAL(icode))
         icode=LIB$FREE_EF(efn)
         if (.not.icode) call LIB$SIGNAL(%VAL(icode))

return
         end

!*****************************************************************
         integer*2 function TTINIT()
!
!        returns communication channel number for terminal-like I/O
!        for example through RS232C ports to the arm and stage.
!
         logical         init,yestemp
         integer*2       ttchan
         integer*4       i,SYS$ASSIGN,icode
         character*60    port
```

```
      data init /.true./
*     This will keep these and only these values
      save init,ttchan
*     around for use each time this routine is called if(init) then
          port='txa4:'
!         call getstr(port,' RS232 port 0-3 ',port,yestemp)
          icode = SYS$ASSIGN(port(:5), ttchan,, )
          If (.not.icode) call LIB$SIGNAL(%VAL(icode))
          init=.false.
      end If
      TTINIT = ttchan
      return
      end
*****************************************************************
      subroutine timer_sub()
      include '($syssrvnam)'
      integer*4 status
      status=sys$wake(,)
      return
      end

*****************************************************************
      subroutine waiter(waist)
      character*5 waist
      include '($syssrvnam)'
      integer*4 interval(2),status external timer_sub
!     print*,'          ...waiting ',waist
      status=sys$bintim('0 :'//waist, interval)
!     print*,'status=',status
      if(.NOT. status) call lib$signal(%val(status))
      status=sys$    setimr( ,'interval ,timer_sub,)
      if(.NOT. status) call lib$signal(%val(status))
      status=sys$hiber()
      if(.NOT. status) call lib$signal(%val(status))
      return
      end

*****************************************************************
      Subroutine MOVEx(oldpos,newpos,drive,ldrvcmmnd,
     2      lcmmnd,trough_unit)

*     Sends a series of pulses to the OM915 to increment stepper
*     motor.  It decides which direction to turn the motor by
*     comparing the old position to new position.

real            oldpos, newpos
      real            pos, time
      logical         yes,long
      integer*4       lcmmnd, trough_unit, q, i,ldrvcmmnd, delta
      character*8     waitasec
      character*60    str
      character*60    drive(3)

*     drive: 1=pulse on/off, 2=CW, 3=CCW
      delta = int(oldpos-newpos)

*     if delta is positive then rotate CCW, if negative then rotate CW
      if (delta.ge.0) call wribot(drive(3) (1: lcmmnd))
      if (delta.lt.0) then
          call wribot(drive(2) (1: lcmmnd))
          delta=delta*(-1)
      end if!delta.lt.0
      if (delta.eq.0) delta=1 waitasec='C:00.01'
      do i = delta, 1, -1
        do q=1, trough_unit
            call wribot(drive(1) (1:ldrvcmmnd))
            call waiter(waitasec)
        end do !q
      end do !i
```

```
              return

End   !MOVEx
***********************************************************
        Subroutine Pump(vlvopn, vlvcls, lcmmnd, pumptm)

*       opens and closes a given valve for time value in PUMPTM real            delta, time, pumptm
        integer*4       lcmmnd
        character*60    vlvopn, vlvcls
        print*,'pumptm=',pumptm
*       open valves
        call wribot(vlvopn(1:lcmmnd))
*       wait for pumptm:
        delta=0
        time=secnds(0.0)
        do while(delta.lt.pumptm)
            delta=secnds(time)
        end do! while

*       close valves
        call wribot(vlvcls (1:lcmmnd))

Return

End  !pump
***********************************************************
        subroutine POSITION_TROUGH(drive, lcmmnd, ldrvcmmnd,
     2                  trough_unit)

*       initializes trough to TCA position and allows user to move trough
*       to any of the active trough positions real*4          oldpos, newpos
        logical         long, check, yescheck
        integer*4       lcmmnd, ldrvcmmnd, trough_unit, i
        character*8     waitasec
        character*60    drive(3), resp

*       position troughs 96      call getstr(resp,'Initialize the trough? (Y/N)','Y',long)
        if ((resp.eq.'N').or.(resp.eq.'n')) goto 97
        if ((resp.eq.'Y').or.(resp.eq.'y')) goto 95
        goto 96

95      print*,'Position troughs so that column 1 is over the TCA trough:'
        print*,' '
        print*,'1. Turn off power to the stepper motor.'
        print*,'2. Push trough unit ALL THE WAY to the left (motor end).'
        print*,'3. Turn on power to the stepper motor.'
        print*,' '
        print*,'NEVER MANUALLY MOVE THE MOTOR WITH POWER ON!'
        print*,' '
        print*,'Make sure that your fingers are out of the way!' call getstr(check,'Press RETURN when done:',yescheck,long)
        call wribot(drive(2) (1:lcmmnd))
        waitasec='0:00.01' do i=1,365      !this puts trough 8 (TCA) under col 1
            call wribot(drive(1) (1:ldrvcmmnd))
            call waiter(waitasec)
        end do !i oldpos=8

97      print*,' '
        print*,'Enter the number which corresponds to positioning'
        print*,'column 1 over the indicated trough:'
        print*,' '
        print*,'pos      col 2   col 1'
        print*,'0.        T       -'
        print*,'1.        G       T'
```

```
            print*,'2.        C       G'
            print*,'3.        A       C'
            print*,'4.        -       A'
            print*,'8.        -       TCA'
            print*,'9.        TCA     -'
            print*,'10.       -       CAP'
            print*,'11.       CAP     -'
            print*,'12.       -       OX'
            print*,'13.       OX      -'
            print*,'14.       Reinitialize trough'
            print*,'999.      Quit'
            print*,' '
            print*,'Unless 14 is entered the trough will automatically'
            print*,'return to position 8 when you exit this routine.'
            print*,' ' call get1real(newpos,'Your choice? Current position:',oldpos)

if (newpos.eq.999) goto 98
            if (newpos.lt.0) goto 97
            if (newpos.eq.14) goto 96
            if (newpos.gt.14) goto 97
            if ((newpos.ge.5).and.(newpos.lt.8)) goto 97
            if (newpos.eq.oldpos) goto 97
            call movex(oldpos,newpos,drive,ldrvcmmnd,lcmmnd,trough_unit)
            oldpos=newpos
            goto 97

98          continue
            if (oldpos.ne.8) then
                    newpos=8
                    call movex(oldpos,newpos,drive,ldrvcmmnd,lcmmnd,
        2           trough_unit)
            end if return end !position_trough

************************************************************************
            subroutine PRIME_REAGENTS(cpureset,lcmmnd,lcpureset,lreset,reset)

*           gives user control over reagent valves.

integer*4       prm, lcmmnd, lreset, lcpureset, i
            logical         yescheck
            character*8     waitasec
            character*60    vacprm, prmvlv, cpureset, reset, check 89          print*,' '
            print*,'Vacuum valve will be open with all reagent selections'
            print*,' '
            print*,'Enter the number corresponding to the valve:'
            print*,'1. tBHP         7. tBHP vacuum    13. tBHP rinse'
            print*,'2. TCA          8. TCA vacuum     14. TCA rinse'
            print*,'3. A monomer    9. A vacuum       15. A rinse'
            print*,'4. C monomer    10.C vacuum       16. C rinse'
            print*,'5. G monomer    11.G vacuum       17. G rinse'
            print*,'6. T monomer    12.T vacuum       18. T rinse'
            print*,' '
            call get1int(prm,'Your choice? 999 to quit',999)

if (prm.eq.999) goto 88 !quit if ((prm.gt.18).or.(prm.lt.1)) goto 89 !input out of range if (prm.lt.7) then !reagent valve
                    write(vacprm,'(a,i2,a)')'#1,SW',prm+6,'=1'
        2           //char(10)//char(13)
                    call wribot(vacprm(1:lcmmnd))
                    write(vacprm,'(a,i2,a)')'#1,SW',prm+6,'=0'
        2           //char(10)//char(13)

end if
```

```
        if (prm.gt.12) then !rinse valve
                write(vacprm,'(a,i2,a)')'#1,SW',prm-6,'=1'
     2          //char(10)//char(13)
                call wribot(vacprm(1:lcmmnd))
                write(vacprm,'(a,i2,a)')'#1,SW',prm-6,'=0'
     2          //char(10)//char(13)
        end if

*       if its anything else:
        write(prmvlv,'(a,i2,a)')'#1,SW',prm,'=1'//char(10)//char(13)
        call wribot(prmvlv(1:lcmmnd))
        write(prmvlv,'(a,i2,a)')'#1,SW',prm,'=0'//char(10)//char(13)
        waitsec='0:01.00'
        call getstr(check,'Hit RETURN to close valve','<CR>',yescheck)
        call wribot(prmvlv(1:lcmmnd))
        call waiter(waitsec)
        call wribot(vacprm(1:lcmmnd))
        goto 89

88      continue return end !prime_reagents

************************************************************************
        subroutine SOLENOIDS(colmax,down,ld,lu,NC,rowmax,up)

*       gives user direct control over individual solenoids integer*4       colmax,rowmax,c,r,NC
        logical         yescheck
        integer*4       lu(colmax,rowmax), ld(colmax,rowmax)
        character*60    up(colmax,rowmax), down(colmax,rowmax)
        character*60    cmmnd print*,' '
        print*,'This routine allows you to control individual solenoids.'
        print*,'All tips will automatically lift when you exit the routine.'
        print*,' '

888     print*,'Enter 999 to quit.'
        call getlint(c,'Column:',999)
        if (c.eq.999)goto 885
        if (c.gt.colmax.or.c.lt.1) then
                print*,'Input out of range.'
                goto 888
        end if 887     call getlint(r,'Row:',1)
        if (r.eq.999)goto 885
        if (r.gt.rowmax.or.r.lt.1) then
                print*,'Input out of range.'
                goto 887
        end if 886     call getstr(cmmnd,'U or D:','U',yescheck)
        if (cmmnd.eq.'999')goto 885
        if ((cmmnd.eq.'U').or.(cmmnd.eq.'u')) then
                call wribot(up(c,r)(1:lu(c,r)))
                goto 888
        end if !up
        if ((cmmnd.eq.'D').or.(cmmnd.eq.'d')) then
                call wribot(down(c,r)(1:ld(c,r)))
                goto 888
        end if !down
        print*,'Input out of range.'
        goto 886

885     do c=1,NC
                do r=1,rowmax
                        call wribot(up(c,r)(1:lu(c,r)))
                end do !r
        end do !c
```

```
884    Continue return end !solenoids
```
************************************************************

What is claimed is:

1. A reactor for sequentially modifying a molecule attached to a solid phase support, comprising
   a plurality of substrate carriers, each substrate carrier capable of carrying a solid phase support to which a molecule to be modified can be attached,
   a plurality of reagent chambers, each capable of comprising a reagent for effecting a modification of said molecule, and
   means for individually bringing each of a plurality of chosen substrate carriers into a reagent-contact mode and a reagent-non-contact mode with each of a plurality of reagent chambers comprising means for individually positioning each of a plurality of chosen substrate carriers in a reagent-contact mode and in a reagent-non-contact mode, and means for positioning each of a plurality of chosen reagent chambers relative to a chosen substrate carrier such that when said chosen substrate carrier is in said reagent-contact mode said chosen substrate carrier is in contact with the contents of a chosen reagent chamber and when said chosen substrate carrier is in said reagent-non-contact mode said chosen substrate carrier is not in contact with said contents of said chosen reagent chamber and wherein said individual positioning means is positioned such that a first substrate carrier and a second substrate carrier can be simultaneously placed in the reagent-contact mode with respect to a first chosen reagent chamber,
   each of a plurality of said substrate carriers being capable of sequential contact with the contents of a plurality of said reagent chambers said sequential contact being capable of resulting in the sequential modification of molecules attached to said solid phase supports on said plurality of substrate carriers.

2. The reactor of claim 1, further comprising means for controlling the sequence in which said plurality of reagent chambers and said plurality of substrate carriers are brought into the reagent-contact mode.

3. The reactor of claim 1, further comprising sufficient reagent chambers to perform a sequence of reactions resulting in the synthesis of a nucleic acid molecule on one of said plurality of substrate carriers.

4. The reactor of claim 1, further comprising sufficient reagent chambers to perform a sequence of reactions resulting in the synthesis of a protein molecule on one of said plurality of substrate carriers.

5. The reactor of claim 1, further comprising means for supplying reagent to and removing reagent from one of said reagent chambers.

6. The reactor of claim 1, further comprising,
   a computer to control the positioning of a plurality of said substrate carriers and the positioning of a plurality of said reagent chambers.

7. The reactor of claim 6, wherein said computer is programmed to effect a sequence of positionings of a first substrate carrier relative to said plurality of reagent chambers said sequence being capable of effecting a desired sequence of modifications of a first polymeric molecule on said first substrate carrier.

8. The reactor of claim 7, wherein said computer is programmed to effect a sequence of positionings of a second substrate carrier relative to said plurality of reagent chambers said sequence being capable of effecting a desired sequence of modifications of a second polymeric molecule in said second substrate carrier.

9. The reactor of claim 8, wherein said computer is programmed such that said first polymeric molecule comprises a different sequence of monomeric subunits than does said second polymeric molecule.

10. The reactor of claim 9, wherein said computer is programmed such that at least one reaction in the modification of said first polymeric molecule and one reaction in the modification of said second polymeric molecule are performed simultaneously.

11. The reactor of claim 10, wherein said computer is programmed such that said simultaneous reactions are performed in different reagent chambers.

12. The reactor of claim 10, wherein said computer is programmed such that said simultaneous reaction are performed in the same reagent chamber.

13. The reactor of claim 1, wherein said means for individually bringing each of a plurality of reagent chambers comprises a moveable carrier which carries a plurality of reagent chambers, said individual positioning means are positioned relative to said moveable carrier such that the action of said individual positioning means causes the transition from the reagent-non-contacting mode to the reagent-contacting mode of a chosen substrate carrier with respect to a chosen one of said reagent chambers and movement of said moveable carrier establishes which of said plurality of reagent chambers is said chosen reagent chamber with respect to a chosen substrate carrier.

14. The reactor of claim 13, wherein said individual positioning means is positioned such that a first substrate carrier and a second substrate carrier can be simultaneously placed in the reagent-contact mode with respect to a first chosen reagent chamber.

15. The reactor of claim 13, further comprising,
   a computer to control the positioning of a plurality of said substrate carriers and the positioning of a plurality of said reagent chambers.

16. The reactor of claim 15, wherein said computer is programmed to effect a sequence of positionings of a first substrate carrier relative to said plurality of reagent chambers said sequence being capable of effecting a desired sequence of modifications of a first polymeric molecule on a first substrate carrier.

17. The reactor of claim 16, wherein said computer is programmed to effect a sequence of positionings of a second substrate carrier relative to said plurality of reagent chambers said sequence being capable of effecting a desired sequence of modifications of a second polymeric molecule in a second substrate carrier.

18. The reactor of claim 17, wherein said computer is programmed such that said first polymeric molecule comprises a different sequence of monomeric subunits than does said second polymeric molecule.

19. The reactor of claim 18, wherein said computer is programmed such that at least one reaction in the modification of said first polymeric molecule and one reaction in the modification of said second polymeric molecule are performed simultaneously.

20. The reactor of claim 19, wherein said computer is programmed such that said simultaneous reactions are performed in different reagent chambers.

21. The reactor of claim 19, wherein said computer is programmed such that said simultaneous reaction are performed in the same reagent chamber.

* * * * *

UNITED STATES PATENT AND TRADEMARK OFFICE
CERTIFICATE OF CORRECTION

PATENT NO.  : 5,288,468
DATED       : Febraury 22, 1994
INVENTOR(S) : George M. Church, Stephen G. Kieffer-Higgins It is certified that error appears in the above-indentified patent and that said Letters Patent is hereby corrected as shown below:

Col. 8, line 42, delete "blocs" and insert --blocks--.
Col. 11, line 23, after "although", insert --small bore--.

Signed and Sealed this

Nineteenth Day of December, 1995

Attest:

BRUCE LEHMAN

Attesting Officer

Commissioner of Patents and Trademarks